US012559729B2

(12) United States Patent (10) Patent No.: US 12,559,729 B2
Wang et al. (45) Date of Patent: Feb. 24, 2026

(54) INDUCTION OF HEPATOCYTES BY STEM CELL DIFFERENTIATION WITH RNA

(71) Applicant: ALLELE BIOTECHNOLOGY AND PHARMACEUTICALS, INC., San Diego, CA (US)

(72) Inventors: Jiwu Wang, La Jolla, CA (US); Yuhui Ni, San Diego, CA (US); Yuanyuan Zhao, San Diego, CA (US)

(73) Assignee: ALLELE BIOTECHNOLOGY AND PHARMACEUTICALS, INC., San Diego, CA (US)

( * ) Notice: Subject to any disclaimer, the term of this patent is extended or adjusted under 35 U.S.C. 154(b) by 0 days.

(21) Appl. No.: 15/815,610

(22) Filed: Nov. 16, 2017

(65) Prior Publication Data

US 2018/0135023 A1 May 17, 2018

Related U.S. Application Data

(60) Provisional application No. 62/423,113, filed on Nov. 16, 2016.

(51) Int. Cl.

| *C12N 5/071* | (2010.01) |
| *A61K 35/407* | (2015.01) |
| *A61K 35/545* | (2015.01) |
| *C12N 5/074* | (2010.01) |

(52) U.S. Cl.
CPC .......... *C12N 5/0696* (2013.01); *A61K 35/407* (2013.01); *A61K 35/545* (2013.01); *C12N 5/067* (2013.01); *C12N 5/0672* (2013.01); *C12N 2310/11* (2013.01); *C12N 2501/60* (2013.01); *C12N 2506/03* (2013.01); *C12N 2506/45* (2013.01); *C12N 2510/00* (2013.01)

(58) Field of Classification Search
CPC .... C12N 5/067; C12N 15/85; C12N 2506/00; C12N 2506/03; C12N 2506/45; C12N 2510/00; A61K 35/407
See application file for complete search history.

(56) References Cited

U.S. PATENT DOCUMENTS

| 2012/0021511 A1 | 1/2012 | D'Amour et al. |
| 2012/0129262 A1 | 5/2012 | West et al. |
| 2012/0190059 A1 | 7/2012 | Deng et al. |
| 2012/0207744 A1 | 8/2012 | Mendlein et al. |
| 2012/0231490 A1* | 9/2012 | Mizuguchi ............. C12N 5/067 |
| | | 435/29 |
| 2013/0029416 A1 | 1/2013 | Thatava et al. |
| 2013/0302295 A1 | 11/2013 | Wang et al. |
| 2014/0087416 A1 | 3/2014 | Simeonov et al. |
| 2014/0315753 A1 | 10/2014 | Guye et al. |
| 2014/0349401 A1 | 11/2014 | Wang et al. |
| 2015/0240235 A1 | 8/2015 | Collombat |

| 2015/0376574 A1 | 12/2015 | Talavera-Adame et al. |
| 2016/0032287 A1 | 2/2016 | Sengupta et al. |
| 2016/0177267 A1 | 6/2016 | Melton |

FOREIGN PATENT DOCUMENTS

| CN | 101541953 A | 9/2009 |
| CN | 102017264 A | 4/2011 |
| CN | 102286535 A | 12/2011 |
| CN | 103037939 A | 4/2013 |
| CN | 103374546 A | 10/2013 |
| CN | 104166316 A | 11/2014 |
| CN | 104520424 A | 4/2015 |
| CN | 104755607 A | 7/2015 |
| CN | 105358680 A | 2/2016 |
| EP | 1885704 A2 | 2/2008 |
| EP | 2532741 A1 | 12/2012 |
| JP | WO-2009157562 A1 | 12/2011 |
| JP | 2012533310 A | 12/2012 |
| JP | 2013252081 A | 12/2013 |
| JP | 2015-527084 A | 9/2015 |
| WO | WO-2004106374 A1 | 12/2004 |
| WO | WO-2006122250 A2 | 11/2006 |
| WO | WO2009137844 A2 | 11/2009 |
| WO | WO-2010136583 A2 | 12/2010 |
| WO | WO2015184318 A1 | 8/2012 |
| WO | WO-2014044646 A1 | 3/2014 |
| WO | WO-2015002724 A2 | 1/2015 |
| WO | WO-2015178397 A1 | 11/2015 |
| WO | WO-2016134313 A1 | 8/2016 |
| WO | WO 2016-187451 A1 | 11/2016 |
| WO | WO2018094111 A1 | 5/2018 |

OTHER PUBLICATIONS

Takayama et al. Molecular Therapy 20(1):127-137, first published online Nov. 8, 2011 (Year: 2011).*
Kim and Eberwine. Anal Bioanal Chem 397:3173-3178, 2010 (Year: 2010).*
Akiyama et al. Development 143:3674-3685, Oct. 2016 (Year: 2016).*
Warren et al. Cell Stem Cell 7:618-630, 2010 (Year: 2010).*
Printout from Innoprot website printed Jan. 25, 2025, p. 1 (Year: 2025).*
Delaforest, Ann et al., HNF4A is essential for specification of hepatic progenitors from human pluripotent stem cells, Development and Stem Cells, 2011, vol. 138, No. 19, pp. 4143-4153.
International Search Report/Written Opinion issued Feb. 22, 2018 in counterpart PCT Application No. PCT/US17/062102.

(Continued)

*Primary Examiner* — Marcia S Noble
(74) *Attorney, Agent, or Firm* — DUANE MORRIS LLP

(57) ABSTRACT

A novel method of inducing or producing hepatocytes from human induced pluripotent stem cells at an unprecedented efficiency and functionality. The core of the invention is the use of experimentally discovered mRNAs at multiple critical differentiation decision points along a pluripotent to mes-endoderm to endoderm to hepatocytes pathway in a previously unknown manner.

22 Claims, 9 Drawing Sheets
(9 of 9 Drawing Sheet(s) Filed in Color)

(56)                    References Cited

OTHER PUBLICATIONS

Si-Tayeb, Karim et al., Organogenesis and development of the liver, Developmental Cell, 2010, vol. 18, pp. 175-189.

Pagliuca, Felicia W., et al. "Generation of functional human pancreatic β cells in vitro." Cell 159.2 (2014): 428-439.

Tsankov, Alexander M., et al. "Transcription factor binding dynamics during human ES cell differentiation." Nature 518.7539 (2015): 344-349.

Jaramillo, Maria, et al. "Potential for pancreatic maturation of differentiating human embryonic stem cells is sensitive to the specific pathway of definitive endoderm commitment." PloS one 9.4 (2014): e94307, 14 pages.

Liu, Jennifer SE, and Matthias Hebrok. "All mixed up: defining roles for β-cell subtypes in mature islets." Genes & Development 31.3 (2017): 228-240.

Clardy, Susan M., et al. "Rapid, high efficiency isolation of pancreatic β-cells." Scientific Reports 5 (2015): 13681, 9 pages.

Kim, Tae Kyung, and James H. Eberwine. "Mammalian cell transfection: the present and the future." Analytical and Bioanalytical Chemistry 397.8 (2010): 3173-3178.

International Search Report/Written Opinion issued Feb. 27, 2018 in counterpart PCT Application No. PCT/US2017/062105, 16 Pages.

Liew, C-G., Generation of Insulin-Producing Cells From Pluripotent Stem cells: From The Selection of Cell Sources to the Optimization of Protocols, The Review of Diabetic Studies, 2010, vol. 7, No. 2, pp. 82-92.

Schiesser, J.V. et al., Derivation of Insulin-producing beta Cells From human pluripotent Stem cells, The Review of Diabetic Studies, 2014, vol. 11, No. 1, pp. 6-18.

Office Action and Search Report in Russian Counterpart Application No. 2019118438, dated Mar. 22, 2021, in 10 pages; English translation provided.

Verhovskaya L.Z. et al., "The effect of glycerin alkoxysubstituent on the morphofunctional properties of a regrafted culture" Cryobiology, 1990 (p. 30-33); English abstract provided.

Office Action in Japan Counterpart Application No. 2019-525968, dated Sep. 21, 2021, in 2 pages; English translation provided.

Office Action in Japan Counterpart Application No. 2019-525963, dated Sep. 14, 2021, in 2 pages; English translation provided.

Badieyan, Zohreh Sadat, and Todd Evans. "Concise review: application of chemically modified mRNA in cell fate conversion and tissue engineering." Stem Cells Translational Medicine 8.8 (2019): 833-843.

Corritore, Elisa, et al. "V-Maf Musculoaponeurotic Fibrosarcoma Oncogene Homolog A Synthetic Modified mRNA Drives Reprogramming of Human Pancreatic Duct-Derived Cells Into Insulin-Secreting Cells." Stem Cells Translational Medicine 5.11 (2016): 1525-1537.

Extended European Search Report in EP Application No. 17872724. 4, dated Oct. 5, 2020, in 9 pages.

Extended European Search Report in EP Application No. 17872174. 2, dated Oct. 28, 2020, in 10 pages.

Guo, Xing Rong, et al. "PDX-1 mRNA-induced reprogramming of mouse pancreas-derived mesenchymal stem cells into insulin-producing cells in vitro." Clinical and Experimental Medicine 15.4 (2015): 501-509, published online Oct. 28, 2014.

Koblas, T., et al. "Reprogramming of Human Pancreatic Organoid Cells into Insulin-Producing β-Like Cells by Small Molecules and in Vitro Transcribed Modified mRNA Encoding Neurogenin 3 Transcription Factor." Folia Biologica 65.3 (2019): 109-123.

Li, Mo, et al. "Cell fate conversion by mRNA." Stem Cell Research & Therapy 2.1 (2011): 5, 3 pages.

Rosa, Alessandro, and Ali H. Brivanlou. "Synthetic mRNAs: powerful tools for reprogramming and differentiation of human cells." Cell Stem Cell 7.5 (2010): 549-550.

Search Report in Singapore Application No. 11201904155W, dated Aug. 10, 2020, in 2 pages.

Search Report in Singapore Application No. 11201904154X, dated Aug. 10, 2020, in 2 pages.

Sauer, Vanessa, et al. "Induced pluripotent stem cells as a source of hepatocytes." Current Pathobiology Reports 2.1 (2014): 11-20.

Warren, Luigi, et al. "Highly efficient reprogramming to pluripotency and directed differentiation of human cells with synthetic modified mRNA." Cell Stem Cell 7.5 (2010): 618-630.

Van Pham, Phuc, et al. "Improved differentiation of umbilical cord blood-derived mesenchymal stem cells into insulin-producing cells by PDX-1 mRNA transfection." Differentiation 87.5 (2014): 200-208.

Warren, Luigi, et al. "Feeder-free derivation of human induced pluripotent stem cells with messenger RNA." Scientific Reports 2 (2012): 657, 7 pages.

Office action in Russian Counterpart Pat. Appln. No. 2019118438, dated Jun. 17, 2022, in 6 pages; English translation provided.

Wang, H., et al. "MAFA controls genes implicated in insulin biosynthesis and secretion." Diabetologia 50.2 (2007): 348-358.

Soria, Bernat. "In-vitro differentiation of pancreatic β-cells." Differentiation 68.4-5 (2001): 205-219.

Wang, Xiao Li, et al. "Gene manipulation of human embryonic stem cells by in vitro-synthesized mRNA for gene therapy." Current Gene Therapy 15.4 (2015): 428-435.

Wang, Xiao Li, et al. "Reprogramming human umbilical cord mesenchymal stromal cells to islet-like cells with the use of in vitro—synthesized pancreatic-duodenal homebox 1 messenger RNA." Cytotherapy, 2014; 16: 1519-1527.

Zhang, Donghui, et al. "Highly efficient differentiation of human ES cells and iPS cells into mature pancreatic insulin-producing cells." Cell Research (2009) 19: 429-438.

Xiaohui Su et al., "How to make hepatocytes by lineage reprogramming" Chemistry of Life, (2016) 4: 449-456; English abstract provided.

Jun, Zhao, et al.. "Three-dimensional culture of porcine hepatocytes for bioartificial liver." Journal of Xi'an Medical University 23.2 (2002): 136-140; English abstract provided.

Search Report in Office action in Chinese Counterpart Pat. Appln. No. 201780071036.0, dated Oct. 26, 2022, in 9 pages.

Search Report in Office action in Chinese Counterpart Pat. Appln. No. 201780071029.0, dated Oct. 26, 2022, in 9 pages.

Zheng, Yang, et al. "Main transcription factors and related mechanisms of embryonic stem cells differentiation into pancreatic endocrine cells." Journal of Clinical Rehabilitative Tissue Engineering Research 14.19 (2010): 3573-3577; English abstract provided.

Li, C. H., et al. "Study of the growth and secretion of microencapsulated pancreatic B cell line in vitro." Zhongguo Ying Yong Sheng li xue za zhi= Zhongguo Yingyong Shenglixue Zazhi= Chinese Journal of Applied Physiology 17.1 (2001): 93-96; English abstract provided.

Hua, Jiang "TAT-PDX1 protein induces the differentiation of human fetal liver mesenchymal stem cells into islet beta cells" Journal of Clinical Rehabilitative Tissue Engineering Research, Jan. 1, 2009 vol. 13, No. 1, 48-52; English abstract provided.

Huang, Yan, et al. "Transcriptome analysis of induced pluripotent stem cell (iPSC)-derived pancreatic β-like cell differentiation." Cell Transplantation 26.8 (2017): 1380-1391.

Mehrabi, Arianeb, et al. "A systematic review of localization, surgical treatment options, and outcome of insulinoma." Pancreas 43.5 (2014): 675-686.

Okabayashi, Takehiro, et al. "Diagnosis and management of insulinoma." World Journal of Gastroenterology: WJG 19.6 (2013): 829, 9 pages.

Davis, Robert L., et al. "Expression of a Single Transfected cDNA Converts Fibroblasts to Myoblasts." Cell, vol. 51, 987-1000, Dec. 24, 1987.

Kajiwara, Masatoshi, et al. "Donor-dependent variations in hepatic differentiation from human-induced pluripotent stem cells." Proceedings of the National Academy of Sciences 109.31 (2012): 12538-12543, with Supporting Information, 9 pages and Correction dated Sep. 4, 2012 in 1 page.

Tapscott, Stephen J., et al. "MyoD1: a nuclear phosphoprotein requiring a Myc homology region to convert fibroblasts to myoblasts." Science 242.4877 (1988): 405-411.

(56)　　　　　　References Cited

OTHER PUBLICATIONS

Tomizawa, Minoru, et al. "Improved Survival and Initiation of Differentiation of Human Induced Pluripotent Stem Cells to Hepatocyte-Like Cells upon Culture in William's E Medium followed by Hepatocyte Differentiation Inducer Treatment." PLoS One 11.4 (2016): e0153435, 20 pages.

Yamamizu, Kohei, et al. "Identification of transcription factors for lineage-specific ESC differentiation." Stem Cell Reports 1.6 (2013): 545-559, with Supplemental Information, 9 pages.
Han, Jianyong, et al. "Tbx3 improves the germ-line competency of induced pluripotent stem cells." Nature 463.7284 (2010): 1096-1100.

\* cited by examiner

Sox17 mRNA

Pax6 mRNA

Mock

INDUCTION OF HEPATOCYTES BY STEM CELL DIFFERENTIATION WITH RNA

CROSS-REFERENCES TO RELATED APPLICATIONS

This application claims the benefit of U.S. Provisional Patent Application No. 62/423,113, filed on Nov. 16, 2016, which is incorporated herein by reference.

FIELD OF THE INVENTION

The present disclosure relates to directing the induction of hepatocytes from pluripotent stem cells through kinetically controlled cell growth processes utilizing specific combinations and ranges of cell density, reagent concentrations, and specific combinations of mRNAs.

BACKGROUND OF THE INVENTION

The recent efforts in the generation and consequent differentiation of human stem cells has changed the paradigms concerning the plasticity of cell fate, models for human diseases, and clinical therapeutics. Both embryonic stem cells (ESCs) and induced pluripotent stem cells (iPSCs) made from somatic cells can be differentiated into an increasing list of specific cell types indistinguishable from their corresponding primary cells. As a result, stem cells are quite promising for developing new human cell therapies. iPSCs show particular potential in the field of personalized medicine because of the unlimited availability of cells, the noninvasiveness of the procedure to obtain the cells, and the potential to immune-match each treatment to individual patients, granting freedom from immunosuppressive drugs.

Lots of research dollars are being spent on developing cell replacement therapies to treat or prevent various human diseases. For example, liver diseases such as liver fibrosis and cirrhosis, which often lead to late stage liver failure, can be treated by transplantation of donated human liver organ or organ-derived hepatocytes. However, finding a reliable supply of donor liver remains a significant hurdle to overcome. Now, many academic and industrial groups have developed ways of directing ESCs or iPSCs to become hepatocytes using multiple recombinant growth factors in the form of recombinant proteins, which are expensive and difficult to control in effective dose.

To alleviate the burden of cost and inconsistency, some researchers have attempted to find small molecules that can influence signal pathways as an agonist or antagonist of growth factor receptors. Although typically less expensive than growth factors, one major disadvantage of small molecules is the non-specific effects they may exert on unintended targets, such as cell membrane-bound receptors, intracellular organelles, or genomic components, etc.

Another key component of a typical differentiation protocol is the media for culturing cells, which may be composed of nutrients (lipids, amino acids, carbohydrates, vitamins, etc.), proper concentrations of salts, pH buffering agents, critical elements, and common protein factors such as insulin or serum albumin. Different types of cells have different requirements of nutrients and media components and is further complicated by cell type specific growth factors and small molecules for signaling.

In clinical applications of stem cell derived tissue cells, most components of the established differentiation media require individual certification under the current good manufacturing practice (cGMP) regulations; for example, growth factors need to be produced by special procedures and require individual certification.

SUMMARY OF THE INVENTION

The present disclosure provides methods for inducing stem cell differentiation by modulating cell growth kinetics and associated parameters whereby specific combination of cells density, reagent concentrations, and combinations of mRNAs are used to control the direction of the differentiation/induction.

To achieve the object and in accordance with the purpose of the invention, as embodied and broadly described herein, one aspect of the invention relates to a method of inducing differentiation of stem cells into hepatocytes, comprising the steps of: (a) culturing induced pluripotent stem cells as starting cells under conditions for differentiation; (b) inducing said starting cells to exit the pluripotent state towards the mesendoderm lineage; (c) directing the differentiating cells towards endoderm cells through culture cell transfection with a first combination of mRNAs at an effective dose and within specific time windows; (d) further directing said endoderm cells towards hepatic progenitor cells through transfection with a second combination of mRNAs; (e) further maturing said hepatic progenitor cells into hepatocytes with a third combination of mRNAs; and (f) obtaining said hepatocytes by passaging progenitor cell clusters into monolayers or collecting clusters formed from said hepatic progenitor cells and replating into monolayers.

In one embodiment, the invention relates to a method of inducing differentiation of stem cells into hepatocytes, comprising the steps of: (a) culturing induced pluripotent stem cells as starting cells under conditions for differentiation; (b) inducing said starting cells to exit the pluripotent state towards the mesendoderm lineage; (c) directing the differentiating cells towards endoderm cells through culture cell transfection with a first combination of mRNAs at an effective dose and within specific time windows; (d) further directing said endoderm cells towards hepatic progenitor cells through transfection with a second combination of mRNAs; (e) further maturing said hepatic progenitor cells into hepatocytes with a third combination of mRNAs; and (f) obtaining said hepatocytes by passaging progenitor cell clusters into monolayers or collecting clusters formed from said hepatic progenitor cells and replating into monolayers, wherein said first combination of mRNAs comprises FoxA2 mRNAs.

In another embodiment, the invention relates to a method of inducing differentiation of stem cells into hepatocytes, comprising the steps of: (a) culturing induced pluripotent stem cells as starting cells under conditions for differentiation; (b) inducing said starting cells to exit the pluripotent state towards the mesendoderm lineage; (c) directing the differentiating cells towards endoderm cells through culture cell transfection with a first combination of mRNAs at an effective dose and within specific time windows; (d) further directing said endoderm cells towards hepatic progenitor cells through transfection with a second combination of mRNAs; (e) further maturing said hepatic progenitor cells into hepatocytes with a third combination of mRNAs; and (f) obtaining said hepatocytes by passaging progenitor cell clusters into monolayers or collecting clusters formed from said hepatic progenitor cells and replating into monolayers, wherein said first combination of mRNAs comprises Sox17 mRNAs.

In another embodiment, the invention relates to a method of inducing differentiation of stem cells into hepatocytes, comprising the steps of: (a) culturing induced pluripotent stem cells as starting cells under conditions for differentiation; (b) inducing said starting cells to exit the pluripotent state towards the mesendoderm lineage; (c) directing the differentiating cells towards endoderm cells through culture cell transfection with a first combination of mRNAs at an effective dose and within specific time windows; (d) further directing said endoderm cells towards hepatic progenitor cells through transfection with a second combination of mRNAs; (e) further maturing said hepatic progenitor cells into hepatocytes with a third combination of mRNAs; and (f) obtaining said hepatocytes by passaging progenitor cell clusters into monolayers or collecting clusters formed from said hepatic progenitor cells and replating into monolayers, wherein said first combination of mRNAs comprises FoxA2 and Sox17 mRNAs.

In another embodiment, the invention relates to a method of inducing differentiation of stem cells into hepatocytes, comprising the steps of: (a) culturing induced pluripotent stem cells as starting cells under conditions for differentiation; (b) inducing said starting cells to exit the pluripotent state towards the mesendoderm lineage; (c) directing the differentiating cells towards endoderm cells through culture cell transfection with a first combination of mRNAs at an effective dose and within specific time windows; (d) further directing said endoderm cells towards hepatic progenitor cells through transfection with a second combination of mRNAs; (e) further maturing said hepatic progenitor cells into hepatocytes with a third combination of mRNAs; and (f) obtaining said hepatocytes by passaging progenitor cell clusters into monolayers or collecting clusters formed from said hepatic progenitor cells and replating into monolayers, wherein said first combination of mRNAs comprises FoxA2, Sox17, GATA4, and GATA6 mRNAs.

In another embodiment, the invention relates to a method of inducing differentiation of stem cells into hepatocytes, comprising the steps of: (a) culturing induced pluripotent stem cells as starting cells under conditions for differentiation; (b) inducing said starting cells to exit the pluripotent state towards the mesendoderm lineage; (c) directing the differentiating cells towards endoderm cells through culture cell transfection with a first combination of mRNAs at an effective dose and within specific time windows; (d) further directing said endoderm cells towards hepatic progenitor cells through transfection with a second combination of mRNAs; (e) further maturing said hepatic progenitor cells into hepatocytes with a third combination of mRNAs; and (f) obtaining said hepatocytes by passaging progenitor cell clusters into monolayers or collecting clusters formed from said hepatic progenitor cells and replating into monolayers, wherein said second combination of mRNAs comprises Hex mRNAs.

In another embodiment, the invention relates to a method of inducing differentiation of stem cells into hepatocytes, comprising the steps of: (a) culturing induced pluripotent stem cells as starting cells under conditions for differentiation; (b) inducing said starting cells to exit the pluripotent state towards the mesendoderm lineage; (c) directing the differentiating cells towards endoderm cells through culture cell transfection with a first combination of mRNAs at an effective dose and within specific time windows; (d) further directing said endoderm cells towards hepatic progenitor cells through transfection with a second combination of mRNAs; (e) further maturing said hepatic progenitor cells into hepatocytes with a third combination of mRNAs; and (f) obtaining said hepatocytes by passaging progenitor cell clusters into monolayers or collecting clusters formed from said hepatic progenitor cells and replating into monolayers, wherein said second combination of mRNAs comprises Tbx3 mRNAs.

In another embodiment, the invention relates to a method of inducing differentiation of stem cells into hepatocytes, comprising the steps of: (a) culturing induced pluripotent stem cells as starting cells under conditions for differentiation; (b) inducing said starting cells to exit the pluripotent state towards the mesendoderm lineage; (c) directing the differentiating cells towards endoderm cells through culture cell transfection with a first combination of mRNAs at an effective dose and within specific time windows; (d) further directing said endoderm cells towards hepatic progenitor cells through transfection with a second combination of mRNAs; (e) further maturing said hepatic progenitor cells into hepatocytes with a third combination of mRNAs; and (f) obtaining said hepatocytes by passaging progenitor cell clusters into monolayers or collecting clusters formed from said hepatic progenitor cells and replating into monolayers, wherein said second combination of mRNAs comprises Tbx3 and Hex mRNAs.

In another embodiment, the invention relates to a method of inducing differentiation of stem cells into hepatocytes, comprising the steps of: (a) culturing induced pluripotent stem cells as starting cells under conditions for differentiation; (b) inducing said starting cells to exit the pluripotent state towards the mesendoderm lineage; (c) directing the differentiating cells towards endoderm cells through culture cell transfection with a first combination of mRNAs at an effective dose and within specific time windows; (d) further directing said endoderm cells towards hepatic progenitor cells through transfection with a second combination of mRNAs; (e) further maturing said hepatic progenitor cells into hepatocytes with a third combination of mRNAs; and (f) obtaining said hepatocytes by passaging progenitor cell clusters into monolayers or collecting clusters formed from said hepatic progenitor cells and replating into monolayers, wherein said second combination of mRNAs comprises Tbx3, GATA4, GATA6, and Hex mRNAs.

In another embodiment, the invention relates to a method of inducing differentiation of stem cells into hepatocytes, comprising the steps of: (a) culturing induced pluripotent stem cells as starting cells under conditions for differentiation; (b) inducing said starting cells to exit the pluripotent state towards the mesendoderm lineage; (c) directing the differentiating cells towards endoderm cells through culture cell transfection with a first combination of mRNAs at an effective dose and within specific time windows; (d) further directing said endoderm cells towards hepatic progenitor cells through transfection with a second combination of mRNAs; (e) further maturing said hepatic progenitor cells into hepatocytes with a third combination of mRNAs; and (f) obtaining said hepatocytes by passaging progenitor cell clusters into monolayers or collecting clusters formed from said hepatic progenitor cells and replating into monolayers, wherein said third combination of mRNAs comprises HNF1a mRNAs.

In another embodiment, the invention relates to a method of inducing differentiation of stem cells into hepatocytes, comprising the steps of: (a) culturing induced pluripotent stem cells as starting cells under conditions for differentiation; (b) inducing said starting cells to exit the pluripotent state towards the mesendoderm lineage; (c) directing the differentiating cells towards endoderm cells through culture cell transfection with a first combination of mRNAs at an effective dose and within specific time windows; (d) further directing said endoderm cells towards hepatic progenitor cells through transfection with a second combination of mRNAs; (e) further maturing said hepatic progenitor cells into hepatocytes with a third combination of mRNAs; and (f) obtaining said hepatocytes by passaging progenitor cell clusters into monolayers or collecting clusters formed from said hepatic progenitor cells and replating into monolayers, wherein said third combination of mRNAs comprises HNF4a mRNAs.

In another embodiment, the invention relates to a method of inducing differentiation of stem cells into hepatocytes, comprising the steps of: (a) culturing induced pluripotent stem cells as starting cells under conditions for differentiation; (b) inducing said starting cells to exit the pluripotent state towards the mesendoderm lineage; (c) directing the differentiating cells towards endoderm cells through culture cell transfection with a first combination of mRNAs at an effective dose and within specific time windows; (d) further directing said endoderm cells towards hepatic progenitor cells through transfection with a second combination of mRNAs; (e) further maturing said hepatic progenitor cells into hepatocytes with a third combination of mRNAs; and (f) obtaining said hepatocytes by passaging progenitor cell clusters into monolayers or collecting clusters formed from said hepatic progenitor cells and replating into monolayers, wherein said third combination of mRNAs comprises HNF4a, HNF1a, HNF6, CEB/Pa, and CEB/Pb mRNAs.

In another embodiment, the invention relates to a method of inducing differentiation of stem cells into hepatocytes, comprising the steps of: (a) culturing induced pluripotent stem cells as starting cells under conditions for differentiation; (b) inducing said starting cells to exit the pluripotent state towards the mesendoderm lineage; (c) directing the differentiating cells towards endoderm cells through culture cell transfection with a first combination of mRNAs at an effective dose and within specific time windows; (d) further directing said endoderm cells towards hepatic progenitor cells through transfection with a second combination of mRNAs; (e) further maturing said hepatic progenitor cells into hepatocytes with a third combination of mRNAs; and (f) obtaining said hepatocytes by passaging progenitor cell clusters into monolayers or collecting clusters formed from said hepatic progenitor cells and replating into monolayers, wherein said starting cells are harvested from a body fluid or tissue.

One aspect of the invention relates to a cell obtained by a method of inducing differentiation of stem cells into hepatocytes, comprising the steps of: (a) culturing induced pluripotent stem cells as starting cells under conditions for differentiation; (b) inducing said starting cells to exit the pluripotent state towards the mesendoderm lineage; (c) directing the differentiating cells towards endoderm cells through culture cell transfection with a first combination of mRNAs at an effective dose and within specific time windows; (d) further directing said endoderm cells towards hepatic progenitor cells through transfection with a second combination of mRNAs; (e) further maturing said hepatic progenitor cells into hepatocytes with a third combination of mRNAs; and (f) obtaining said hepatocytes by passaging progenitor cell clusters into monolayers or collecting clusters formed from said hepatic progenitor cells and replating into monolayers.

One aspect of the invention relates to a composition for treating disease, disorder, or malformation, comprising a cell obtained by a method of inducing differentiation of stem cells into hepatocytes, comprising the steps of: (a) culturing induced pluripotent stem cells as starting cells under conditions for differentiation; (b) inducing said starting cells to exit the pluripotent state towards the mesendoderm lineage; (c) directing the differentiating cells towards endoderm cells through culture cell transfection with a first combination of mRNAs at an effective dose and within specific time windows; (d) further directing said endoderm cells towards hepatic progenitor cells through transfection with a second combination of mRNAs; (e) further maturing said hepatic progenitor cells into hepatocytes with a third combination of mRNAs; and (f) obtaining said hepatocytes by passaging progenitor cell clusters into monolayers or collecting clusters formed from said hepatic progenitor cells and replating into monolayers.

One aspect of the invention relates to a method of treating disease, disorder, or malformation, comprising the step of administering into the subject in need thereof at least one of a cell obtained by a method of inducing differentiation of stem cells into hepatocytes, comprising the steps of: (a) culturing induced pluripotent stem cells as starting cells under conditions for differentiation; (b) inducing said starting cells to exit the pluripotent state towards the mesendoderm lineage; (c) directing the differentiating cells towards endoderm cells through culture cell transfection with a first combination of mRNAs at an effective dose and within specific time windows; (d) further directing said endoderm cells towards hepatic progenitor cells through transfection with a second combination of mRNAs; (e) further maturing said hepatic progenitor cells into hepatocytes with a third combination of mRNAs; and (f) obtaining said hepatocytes by passaging progenitor cell clusters into monolayers or collecting clusters formed from said hepatic progenitor cells and replating into monolayers and a composition for treating disease, or malformation, comprising a cell obtained by a method of inducing differentiation of stem cells into hepatocytes, comprising the steps of: (a) culturing induced pluripotent stem cells as starting cells under conditions for differentiation; (b) inducing said starting cells to exit the pluripotent state towards the mesendoderm lineage; (c) directing the differentiating cells towards endoderm cells through culture cell transfection with a first combination of mRNAs at an effective dose and within specific time windows; (d) further directing said endoderm cells towards hepatic progenitor cells through transfection with a second combination of mRNAs; (e) further maturing said hepatic progenitor cells into hepatocytes with a third combination of mRNAs; and (f) obtaining said hepatocytes by passaging progenitor cell clusters into monolayers or collecting clusters formed from said hepatic progenitor cells and replating into monolayers.

In another embodiment, the invention relates to a method of treating disease, disorder, or malformation, comprising the step of administering into the subject in need thereof at least one of a cell obtained by a method of inducing differentiation of stem cells into hepatocytes, comprising the steps of: (a) culturing induced pluripotent stem cells as starting cells under conditions for differentiation; (b) inducing said starting cells to exit the pluripotent state towards the mesendoderm lineage; (c) directing the differentiating cells towards endoderm cells through culture cell transfection with a first combination of mRNAs at an effective dose and within specific time windows; (d) further directing said endoderm cells towards hepatic progenitor cells through transfection with a second combination of mRNAs; (e) further maturing said hepatic progenitor cells into hepatocytes with a third combination of mRNAs; and (f) obtaining said hepatocytes by passaging progenitor cell clusters into monolayers or collecting clusters formed from said hepatic progenitor cells and replating into monolayers and a composition for treating disease, or malformation, comprising a cell obtained by a method of inducing differentiation of stem cells into hepatocytes, comprising the steps of: (a) culturing induced pluripotent stem cells as starting cells under conditions for differentiation; (b) inducing said starting cells to exit the pluripotent state towards the mesendoderm lineage; (c) directing the differentiating cells towards endoderm cells through culture cell transfection with a first combination of mRNAs at an effective dose and within specific time windows; (d) further directing said endoderm cells towards hepatic progenitor cells through transfection with a second combination of mRNAs; (e) further maturing said hepatic progenitor cells into hepatocytes with a third combination of mRNAs; and (f) obtaining said hepatocytes by passaging progenitor cell clusters into monolayers or collecting clusters formed from said hepatic progenitor cells and replating into monolayers, wherein said cell is derived from the recipient subject.

In another embodiment, the invention relates to a method of treating disease, disorder, or malformation, comprising the step of administering into the subject in need thereof at least one of a cell obtained by a method of inducing differentiation of stem cells into hepatocytes, comprising the steps of: (a) culturing induced pluripotent stem cells as starting cells under conditions for differentiation; (b) inducing said starting cells to exit the pluripotent state towards the mesendoderm lineage; (c) directing the differentiating cells towards endoderm cells through culture cell transfection with a first combination of mRNAs at an effective dose and within specific time windows; (d) further directing said endoderm cells towards hepatic progenitor cells through transfection with a second combination of mRNAs; (e) further maturing said hepatic progenitor cells into hepatocytes with a third combination of mRNAs; and (f) obtaining said hepatocytes by passaging progenitor cell clusters into monolayers or collecting clusters formed from said hepatic progenitor cells and replating into monolayers and a composition for treating disease, or malformation, comprising a cell obtained by a method of inducing differentiation of stem cells into hepatocytes, comprising the steps of: (a) culturing induced pluripotent stem cells as starting cells under conditions for differentiation; (b) inducing said starting cells to exit the pluripotent state towards the mesendoderm lineage; (c) directing the differentiating cells towards endoderm cells through culture cell transfection with a first combination of mRNAs at an effective dose and within specific time windows; (d) further directing said endoderm cells towards hepatic progenitor cells through transfection with a second combination of mRNAs; (e) further maturing said hepatic progenitor cells into hepatocytes with a third combination of mRNAs; and (f) obtaining said hepatocytes by passaging progenitor cell clusters into monolayers or collecting clusters formed from said hepatic progenitor cells and replating into monolayers, wherein said starting cells are harvested from the recipient.

One aspect of the invention relates to a method of producing differentiated hepatocytes from induced pluripotent stem cells, comprising the steps of: (a) culturing said induced pluripotent stem cells as starting cells under conditions for differentiation; (b) inducing said starting cells to exit the pluripotent state towards the mesendoderm lineage; (c) directing the differentiating cells towards endoderm cells through culture cell transfection with a first combination of mRNAs at an effective dose and within specific time windows; (d) further directing said endoderm cells towards hepatic progenitor cells through transfection with a second combination of mRNAs; (e) further maturing said hepatic progenitor cells into hepatocytes with a third combination of mRNAs; and (f) obtaining said hepatocytes by passaging progenitor cell clusters into monolayers or collecting clusters formed from said hepatic progenitor cells and replating into monolayers.

One aspect of the invention relates to a method for producing endoderm cells from induced pluripotent stem cells, comprising the steps of: (a) culturing said induced pluripotent stem cells as starting cells under conditions for differentiation; (b) inducing said starting cells to exit the pluripotent state towards the mesendoderm lineage; and (c) directing the differentiating cells towards endoderm through culture cell transfection with endoderm-specific mRNAs at an effective dose and within specific time windows.

In one aspect, this disclosure provides novel, enabling processes relating to managing cell density and rate of division to achieve desired differentiation results. In some aspects, the processes include, for example, optimization of timing, order of addition, RNA doses and ratios among different RNAs during transfection of RNAs, and their duration or number of repeats. In some aspects, the invention further relates to the choices of surface of culture vessels and environmental conditions such as oxygen concentration. This disclosure further provides processes and methods of selection of desired cells or enhancement of their percentage in the overall population, and methods of cryopreservation and re-culture of differentiated cells. The methods of this disclosure include streamlined protocols and efficient methods of maturing hepatocytes through a 3-dimensional stage. In some aspects the mature, differentiated hepatocytes produced from manipulating stem cells secrete glycogen. In one aspect, the current invention provides a newly developed protocol that produces more functional and more mature hepatocytes that function in vivo. In some aspects the mature hepatocytes of this disclosure are useful for therapies of various liver diseases, conditions and injuries.

In certain embodiments, the exemplary method of producing mature and functional hepatocytes through stem cell induction can be represented by the regimen and steps as described and set forth in the examples herein. By contacting mRNA with cells at critical fate changing points at the right dose and delivery conditions, very high efficiency was achieved, and at lower costs without using large amount of expensive growth factors. Because mRNAs are more specific in directing cellular and developmental events via encoding functional proteins, the disclosed method is much more robust than any known methods in producing human liver cells, paving a way for human therapies in treating liver diseases, conditions and injuries.

In some aspects, the present disclosure also provides novel methods of achieving cell fate determination without using, or using reduced amounts of small molecules that influence signal pathways as an agonist or antagonist of growth factor receptors, which often vary in purity, stability, and toxicity.

In another aspect of the current disclosure, the methods provide a major benefit in the simplicity of establishing differentiation medium through use of properly supplied mRNAs of differentiation-directing genes. This is in contrast to the prior approach of painstaking testing of "differentiation medium" by removing or adding one component at a time. In one aspect, the optimal combination of mRNAs and appropriate medium, as well as other parameters disclosed herein can streamline the process of producing differentiated, functional hepatocytes, and is an integral part of the current invention.

In addition, other methods also rely on animal products such as serum or Matrigel which must undergo certification and/or which must be produced using GMP practices. Another aspect of the current invention is to create a new method that is primarily based on a single type of molecule suitable for uniform certification and quality control processes.

The present disclosure provides differentiation methods that utilize highly efficient and well-controlled expression of master control genes or key transcription factors in tissue specific differentiation. More specifically, these factors are introduced into pluripotent stem cells in the form of properly modified and purified mRNA molecules demonstrated through the provided exemplar.

In one aspect, the present disclosure provides a method of inducing cell differentiation comprising: utilizing key cell fate factors and fusions between conventional transcription factors (TFs) with transactivation domains, optimized for directing stem cells towards different types of cells; introducing these factors as synthetic messenger RNA (mRNA) into cultured pluripotent stem cells at the preferred density by methods that result in appropriate levels of transgene expression; maintaining cells under optimized conditions to result in high efficiency of specific differentiation whereby the pluripotent state or progenitor state of stem cells or progenitor cells is induced towards a specific lineage or tissue cell type.

In another aspect, the disclosure provides methods for changing the pluripotent state or progenitor state of stem cells or progenitor cells towards a specific lineage or tissue cell type, comprising at least one of: generating stem cells expressing critical cell fate genes (collectively referred as stem cells), including key cell fate factors and fusions between conventional transcription factors (TFs) with transactivation domains, optimized for directing stem cells towards different types of cells; introducing these factors as synthetic messenger RNA (mRNA) into cultured pluripotent stem cells at the preferred density by methods that result in appropriate levels of transgene expression; maintaining cell under optimized conditions to result in high efficiency of specific differentiation.

In one aspect, the present disclosure provides a method for producing differentiated hepatocytes from iPSCs, the method comprising: a) culturing iPSCs as starting cells under experimentally verified conditions as disclosed herein, prepare the cells as starting cells for differentiation; b) inducing the starting cells to exit the pluripotent state towards the mesendoderm lineage; c) directing the differentiating cells towards endoderm by using endoderm specifying genes' mRNA through culture cell transfection at disclosed dose and within the specific time windows; d) further directing the endoderm cells towards hepatic progenitor cells using a further gene's or a combination of genes' mRNA molecules through transfection; e) further maturing the hepatic progenitor cells into hepatocytes with yet another gene's or combination of genes' mRNAs; f) obtain hepatocytes by passaging progenitor cell clusters into monolayers or collecting clusters formed from hepatic progenitor cells and replating into monolayers.

In one aspect, the present disclosure provides a method for producing endoderm cells from iPSCs, the method comprising: a) culturing iPSCs as starting cells under experimentally verified conditions as disclosed herein, prepare the cells as starting cells for differentiation; b) inducing the starting cells to exit the pluripotent state towards the mesendoderm lineage; c) directing the differentiating cells towards endoderm by using endoderm specifying genes' mRNA through culture cell transfection at disclosed dose and within the specific time windows.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing aspects and advantages of this invention may become apparent from the following detailed description with reference to the accompanying drawings in which:

FIG. 2 shows hepatic progenitor cells started from different endoderm cell densities forming clusters and illustrates an exemplary embodiment of hepatic progenitor induction.

FIG. 5 shows cells in hepatocyte spheres (H&E on the left) are positive for glycogen (PAS on the right) and illustrates an exemplary embodiment of hepatocytes in 3D that function in secreting glycogen.

FIG. 6 shows cells in hepatocyte spheres displaying hepatocyte markers and illustrates an exemplary embodiment of endoderm and hepatocytes derived from human iPSCs displaying specific cell markers.

FIG. 8 shows two million iPSCs in the starting population were transfected using MaxCyte STX, set at Optimization 2, OC-100 processing assembly. Photos were taken 24 hours post-transfection using an EVOS imaging system at 10×.

DETAILED DESCRIPTION OF THE INVENTION

Figure 1A:
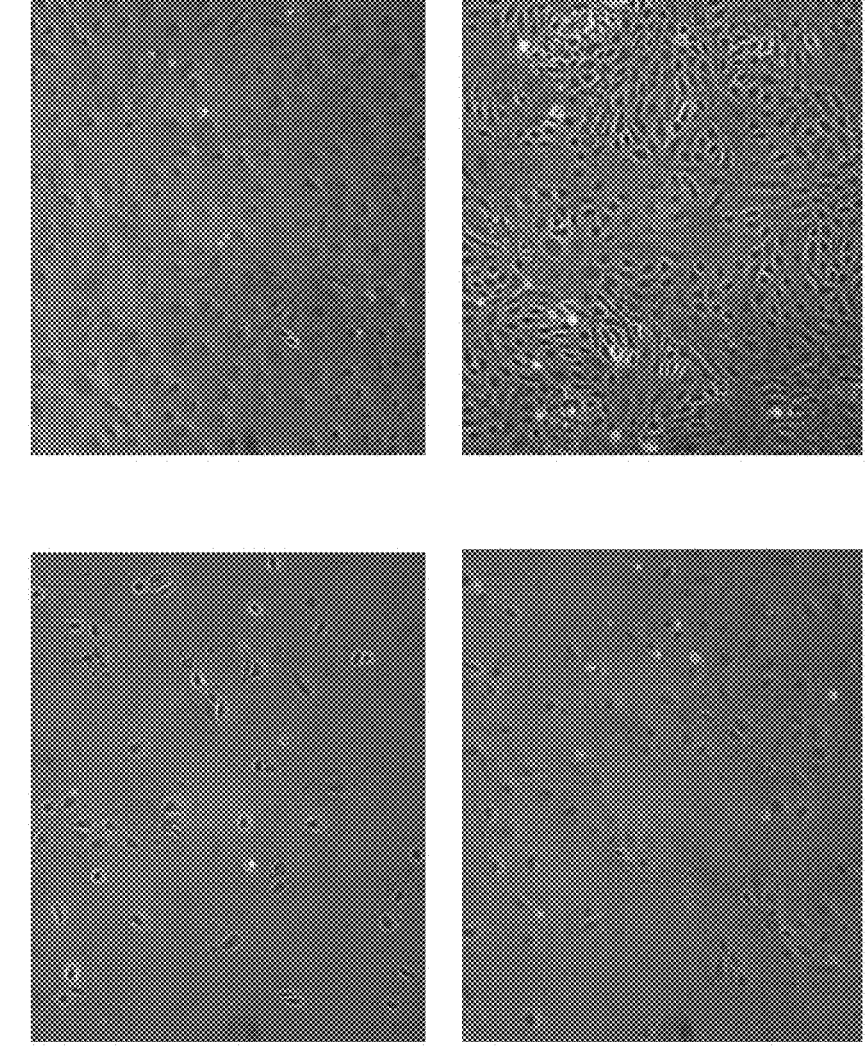
FIG. 1A shows endoderm cells from different starting densities and illustrates an exemplary embodiment of endoderm induction.

When describing the present invention, all terms not defined herein have their common meanings recognized in the art. To the extent that the following description is of a specific embodiment or a particular use of the invention, it is intended to be illustrative only, and not limiting of the claimed invention. The following description is intended to cover all alternatives, modifications and equivalents that are included in the spirit and scope of the invention.

The concept of that a "master control" gene, i.e. one key gene (typically a transcription factor gene, sometimes a small number of genes working together) can decide the fate of cells and tissues and eventually the formation of an entire organ during development, has been generally accepted based on studies in muscle (MyoD), eye (Pax6), and other fields of developmental biology. Shinya Yamanaka's discovery that differentiated cells can be reverted to a pluripotent state by the expression of a select group of transcription factors expressed in stem cells demonstrated the power of a small number of key transcription factors in driving cells through a lengthy, multi-stage fate change. Work by other groups on iPSC generation expanded the choices of reprogramming factors and showed that some variations can be tolerated in transcription factor choices for the purpose of reprogramming. In Yamanaka's original work, expression of the reprogramming factors was achieved through the application of viral vectors which integrate into the genome because prolonged expression of these factors is required to effect cell transformation. The attendant modification of the genome represents an important hurdle to therapeutic application of iPSCs, while the possibility of reactivated expression from integrated viral cassettes is a concern even for in vitro studies. The application of mRNA transfection to reprogramming as most recently disclosed by the current inventor group is particularly appealing as this system allows the expression of reprogramming cocktails and even individual component factors to be modulated in short time frames simply by changing which transcripts are added to the cell culture media. Once transfection of a particular factor is terminated, ectopic expression within the target cells ceases quickly due to the rapid decay of mRNA in the cytoplasm. Even though mRNA does not persist in the target cell, its ability to be directly translated in the cytoplasm, without the need of rate-limiting nuclear translocation as in the case of transfected DNA and integrating viral vectors, more than compensate for mRNA's short half-life to result in highly efficient expression but well within a small time window, which is critical for cell fate determination.

Long-lasting DNA vectors, such as episomal plasmids, when used for cell fate alteration, require weaning to reduce any risk of random genomic integration. RNA viruses or virus-derivatives, such as the Sendai virus or Venezuelan equine encephalitis (VEE) virus, even after being stripped to be a modified noninfectious RNA replicon, still carries viral elements, prone to recombination with viral elements hidden in the host genome. It is always difficult to be completely sure that the cells are rid of the viral vectors without tedious finding of proof in the form of negative data. The current invention discloses multiple inventive steps aimed at applying the advantages of mRNA-based cell fate determination to directed differentiation. In summary, the current disclosure teaches a single or multiple rounds of ectopic transcription factor expression in a streamlined method to direct cell differentiation.

Nonetheless, there are technical barriers to mRNA-based stem cell differentiation. Not all stem cell types and culture media are equally conducive to efficient mRNA delivery, and this is currently an impediment to mRNA-based differentiation. It has also been commonly known that stem cells, particularly most human stem cell lines, are rather difficult to culture without forming transfection-resistant patches. It is part of the current invention's teaching that pluripotent stem cells can be grown under conditions that most of the cells can be transfected with modified mRNAs. In another embodiment, the dose of RNA and transfection reagent (both of which have associated toxicities) are to be provided to the cells at levels capable of exerting master control gene effects while supporting the viability of the target cells in the face of the pro-apoptotic and cytostatic forces engendered by the cell fate changing process.

Accordingly, in view of the problems associated with the previously known stem cell differentiation procedures, the novel methods, materials, and protocols described herein produce different cell types from iPSCs or ESCs with improved efficiency of the process and quality of the resultant cells. The current invention achieved significant improvements through potentiation of the TF mRNA delivered to the target stem cells. The current invention also provides novel protocols which support the production of footprint-free tissue cells from human stem cells without the use of feeder cells or any other potentially xeno-contaminated reagents. The new protocols extend the benefits of the modified mRNA and help clear remaining roadblocks to the therapeutic application of stem cell derivation technology.

Given that differentiation from pluripotent to terminally differentiated state often takes multiple steps, requiring a time frame of several weeks to even months, the growth factor-based, stepwise strategy is intrinsically inefficient and tedious. Accordingly, embodiments of the present invention fundamentally remove the need for growth factors in guiding generation of hepatocytes.

More specifically, this invention relates to changing the pluripotent state or progenitor state of stem cells or progenitor cells towards a specific lineage or tissue cell type by expressing critical cell fate genes (collectively referred as stem cells), including key cell fate factors and fusions between conventional transcription factors (TFs) with trans-activation domains, optimized for directing stem cells towards different types of cells; introducing these factors as synthetic messenger RNA (mRNA) into cultured pluripotent stem cells at the preferred density by methods that result in appropriate levels of transgene expression; maintaining cells under optimized conditions to result in previously unattainable efficiency of specific differentiation. Factors expressed through introduction of mRNA can also include growth factors, cytokines, hormones, signal peptides and other cell fate influencing secreted factors or modifying enzymes. Using similar procedure, microRNAs (miRNAs) or other non-protein-coding RNAs can be introduced into cells under cell state transition in order to direct differentiation. Compared to other methods that are known in the art, the current invention dramatically reduces the time, cost, and effort involved in stem cell differentiation into hepatocytes.

This invention describes a method of changing the pluripotent state or progenitor state of stem cells or progenitor cells towards a specific lineage or tissue cell type, comprising at least one of: expressing critical cell fate genes, including key cell fate factors, and optimized for directing stem cells towards different types of cells; introducing these factors as synthetic messenger RNA (mRNA) into cultured pluripotent stem cells at the preferred density by methods that result in appropriate levels of transgene expression; maintaining cell under optimized conditions to result in high efficiency of specific differentiation.

In certain embodiments, the fully stabilized, expanded iPSCs are provided.

In certain embodiments, there is no need to clear episomes or RNA virus (e.g., Sendai), which can take 10+ passages of iPSCs post-isolation.

In certain embodiments, the process is feeder-free.

In certain embodiments, the process is xeno-free, comprising all synthetic or human reagents and no non-human animal-derived components.

In certain embodiments, the process is footprint-free: having no random integration of DNA into genome (as often happens with episomal).

In certain embodiments, the process yields a fully-customized genetic background via patient-specific starting tissue and/or genome-editing.

Figures 8A, 8B, 8C, 8D, 8E, 8F:
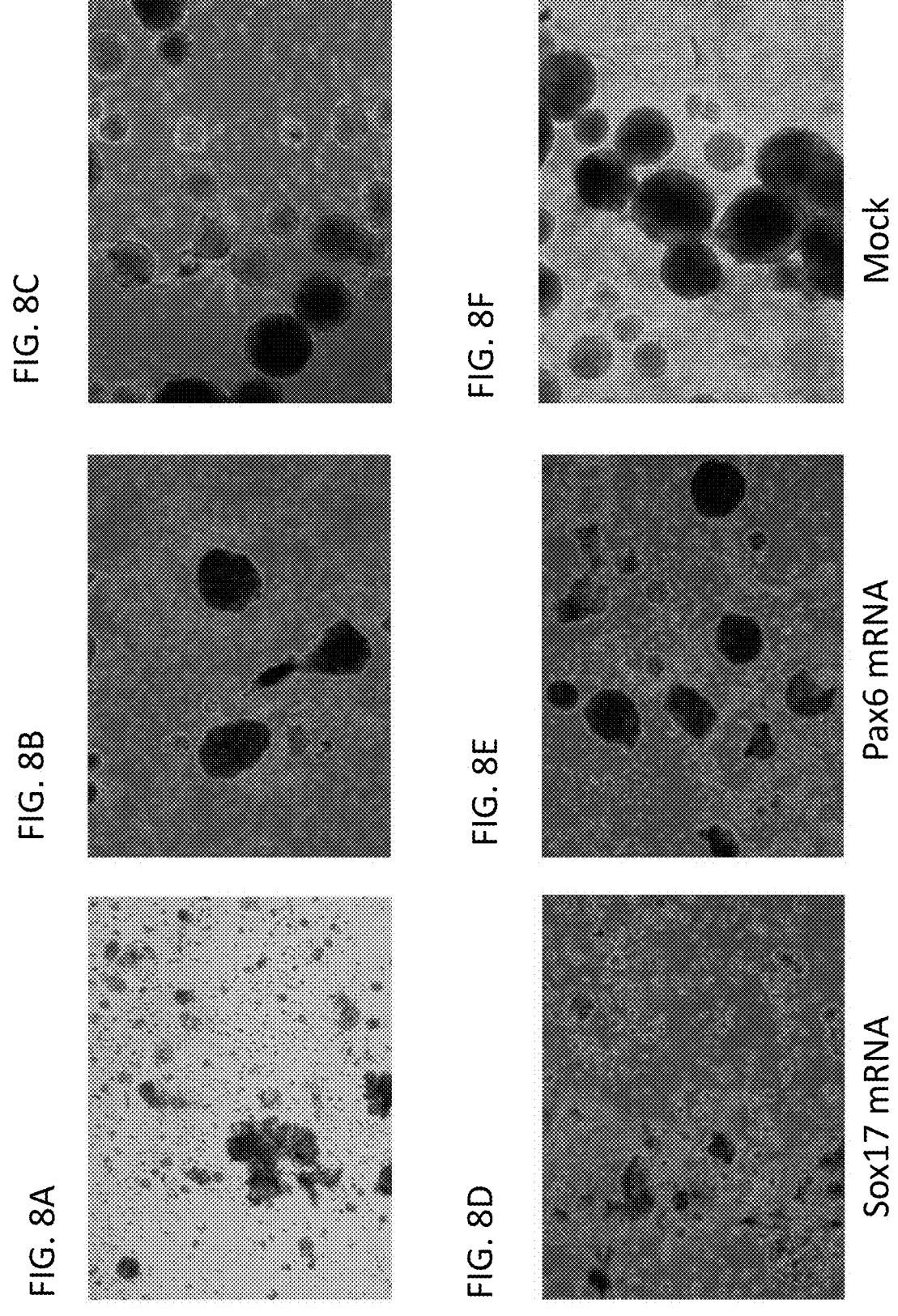
FIG. 8A shows an exemplary view of the iPSC associated with the exemplary transfection.
FIG. 8B shows an exemplary view of the iPSC associated with the exemplary transfection.
FIG. 8C shows an exemplary view of the iPSC associated with the exemplary transfection.
FIG. 8D shows an exemplary view of the iPSC associated with the exemplary transfection.
FIG. 8E shows an exemplary view of the iPSC associated with the exemplary transfection.
FIG. 8F shows an exemplary view of the iPSC associated with the exemplary transfection.

In another experiment, as an alternative to the process outlined in Table 1, iPSC cells grown as spheres in suspension were transfected directly using electroporation, (for example, using MaxCyte STX electroporator) without plating on the surface of a plate. In one embodiment, 2 million starting iPSCs in spheres were transfected in suspension with different mRNA, e.g. Sox17 or Pax6, or mock transfected. The mRNA amount tested in FIG. 8 was 2500 ng. Cells were then grown in NBM in the case of Sox17 transfection, or MEMalpha with KSR in the case of Pax6 transfection. Transfection can be repeated 1, 2, 3, 4, 5 or even more times if the transition takes longer period of time. As result, after the $1^{st}$ transfection of Sox17 mRNA, the cell clusters became significantly smaller and less compact spheres, losing defined "edge" or outer boundary. In contrast, mock-transfected spheres maintain well-defined, showing clearly visible outer "edge" in 2D photos. The smaller spheres of the untransfected or mock-transfected iPSCs have a transparent appearance, whereas the bigger ones look less transparent for being thick in cell layers. For comparison, iPSC spheres transfected with Pax6 (a neural differentiation TF) mRNA progressed towards ectoderm, i.e. neural progenitor cells, of which the spheres became darker and had less sharp "edge" than mock-transfected, but were bigger in size and had more defined boundaries than the Sox17 transfected.

By the same principle and similar methods, germ layer-specific intermediate cells such as endoderm cells, and more downstream intermediate cells such as hepatocyte progenitor cells, pancreatic progenitor cells, etc., can also be transfected with additional TF mRNAs in spheres. Cells transfected this way are more resistant to toxicity from small molecules, growth factors, or other elements in cell cultures, and should be in general more efficient in differentiation than 2D transfection using chemical reagents. This observation, unseen in scientific publication, was made inadvertently during a testing of an electroporation equipment, and served as an enabling method as part of the current disclosure.

Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The term "hepatocyte-like cell" is intended to mean a cell sharing features with a hepatocyte. Hepatocyte-like cells are further defined by morphological characteristics as well as by specific marker characteristics. As induced pluripotent stem cell-derived hepatocyte-like cells share similar characteristics (including marker and hormonal characteristics) with hepatocytes, induced pluripotent stem cell-derived hepatocyte-like cells may be used interchangeably with induced pluripotent stem cell-derived liver cell or hepatocytes.

An "embryoid body" refers to an aggregate of cells derived from pluripotent cells, where cell aggregation can be initiated by any method that prevents the cells from adhering to a surface to form typical colony growth. As used herein, "embryoid body" refers to a three-dimensional spheroid aggregate of pluripotent stem cells, including but not limited to embryonic stem cells derived from the blastocyst stage of embryos from mammalian sources. An embryoid body can be formed from embryonic stem cells derived through any technique generally known in the art, including but not limited to somatic cell nuclear transfer or the reprogramming of somatic cells to yield induced pluripotent stem cells.

As used herein, the term "induced pluripotent stem cells" refers to a pluripotent stem cell derived from a somatic cell (e.g. an adult somatic cell). Induced pluripotent stem cells are similar to embryonic stem cells in their differentiation abilities to form any adult cell types, but are not derived from an embryo.

As used herein, "cell," "cell line," and "cell culture" include progeny. It is also understood that all progeny may not be precisely identical in DNA content, due to deliberate or inadvertent mutations. Variant progeny that have the same function or biological property, as screened for in the originally transformed cell, are included.

As used herein, "composition" refers to a combination of active agent and at least one other compound or molecule, inert (for example, a detectable agent or label) or active, such as an adjuvant.

As used herein, "culturing" refers to maintaining cells under conditions in which they can proliferate and avoid senescence as a group of cells. "Culturing" can also include conditions in which the cells also or alternatively differentiate.

As used herein, "differentially expressed," refers to the differential production of RNA, including but not limited to mRNA, tRNA, miRNA, siRNA, snRNA, and piRNA transcribed from a gene or regulatory region of a genome or the protein product encoded by a gene as compared to the level of production of RNA by the same gene or regulator region in a normal or a control cell. In another context, "differentially expressed," also refers to nucleotide sequences or proteins in a cell or tissue which have different temporal and/or spatial expression profiles as compared to a normal or control cell.

As used herein, "overexpressed" or "overexpression" refers to an increased expression level of an RNA or protein product encoded by a gene as compared to the level of expression of the RNA or protein product in a normal or control cell.

As used herein, "underexpressed" or "underexpression" refers to decreased expression level of an RNA or protein product encoded by a gene as compared to the level of expression of the RNA or protein product in a normal or control cell.

As used herein, "differentiate" or "differentiation," refers to the process by which precursor or progenitor cells (i.e., hepatic progenitor cells) differentiate into specific cell types, e.g., hepatocytes.

As used herein, "effective amount" is an amount sufficient to effect beneficial or desired biological, emotional, medical, or clinical response of a cell, tissue, system, animal, or human. An effective amount can be administered in one or more administrations, applications, or dosages. The term also includes, within its scope, amounts effective to enhance normal physiological function.

As used herein, "expansion" or "expanded" in the context of cells, refers to an increase in the number of a characteristic cell type, or cell types, from an initial population of cells, which may or may not be identical. The initial cells used for expansion need not be the same as the cells generated from expansion. For instance, the expanded cells may be produced by ex vivo or in vitro growth and differentiation of the initial population of cells.

As used herein, "expression" refers to the process by which polynucleotides are transcribed into RNA transcripts. In the context of mRNA and other translated RNA species, "expression" also refers to the process or processes by which the transcribed RNA is subsequently translated into peptides, polypeptides, or proteins.

As used herein, "induced pluripotent stem cell" or "iPS cell" or "iPSC" refers to a cell capable of differentiating into multiple cell types that is artificially derived (not naturally derived) from a non-pluripotent cell.

As used herein, "integration free iPS cell" refers to an iPS cell that does not contain an exogenous transgene integrated into the genome of the non-pluripotent cell.

As used herein, "isolated" means separated from constituents, cellular and otherwise, in which the polynucleotide, peptide, polypeptide, protein, antibody, or fragments thereof, are normally associated with in nature. A non-naturally occurring polynucleotide, peptide, polypeptide, protein, antibody, or fragments thereof, do not require "isolation" to distinguish it from its naturally occurring counterpart.

As used herein, "concentrated" refers to a molecule, including but not limited to a polynucleotide, peptide, polypeptide, protein, antibody, or fragments thereof, that is distinguishable from its naturally occurring counterpart in that the concentration or number of molecules per volume is greater than that of its naturally occurring counterpart.

As used herein, "diluted" refers to a molecule, including but not limited to a polynucleotide, peptide, polypeptide, protein, antibody, or fragments thereof, that is distinguishable from its naturally occurring counterpart in that the concentration or number of molecules per volume is less than that of its naturally occurring counterpart.

As used herein, "separated" refers to the state of being physically divided from the original source or population such that the separated compound, agent, particle, or molecule can no longer be considered part of the original source or population.

As used herein, "mammal," for the purposes of treatments, refers to any animal classified as a mammal, including human, domestic and farm animals, nonhuman primates, and zoo, sports, or pet animals, such as, but not limited to, dogs, horses, cats, and cows.

As used herein, "stem cell" refers to any self-renewing totipotent, pluripotent cell or multipotent cell or progenitor cell or precursor cell that is capable of differentiating into multiple cell types.

As used herein, "totipotent" refers cells that can differentiate and give rise to all cells types in an organism, plus the extraembryoinc, or placental, cells.

As used herein, "pluripotent" refers to cells that can differentiate and give rise to all of the cell types that make up an organism, including any fetal or adult cell type, except for the extraembryonic, or placental, cells.

As used herein, "multipotent" refers to cells that can develop into more than one cell type, but are more limited than pluripotent cells in the cell types that they can develop into.

As used interchangeably herein, "subject," "individual," or "patient" refers to a vertebrate organism.

As used herein, "substantially pure cell population" refers to a population of cells having a specified cell marker characteristic and differentiation potential that is about 50%, preferably about 75-80%, more preferably about 85-90%, and most preferably at least about 95% of the cells making up the total cell population. Thus, a "substantially pure cell population" refers to a population of cells that contain fewer than about 50%, preferably fewer than about 20-25%, more preferably fewer than about 10-15%, and most preferably fewer than about 5% of cells that do not display a specified marker characteristic and differentiation potential under designated assay conditions.

As used herein, "pre-differentiation" refers to the process by which precursor or progenitor cells (e.g., pluripotent stem cells) differentiate into intermediate cell types, e.g., hepatic progenitor cells, which have the potential to differentiate further to final effector cells (e.g. hepatocytes).

As used herein, "therapeutic" refers to treating, healing, and/or ameliorating a disease, disorder, condition, or side effect, or to decreasing in the rate of advancement of a disease, disorder, condition, or side effect. The term also includes within its scope enhancing normal physiological function, palliative treatment, and partial remediation of a disease, disorder, condition or side effect.

The terms "treating" and "treatment" as used herein refer generally to obtaining a desired pharmacological and/or physiological effect. The effect may be prophylactic in terms of preventing or partially preventing a disease, symptom or condition thereof, and/or may be therapeutic in terms of a partial or complete cure of a disease, condition, symptom, or adverse effect attributed to the disease. The term "treatment" as used herein covers any treatment in a mammal, particularly a human, and includes: (a) preventing the disease from occurring in a subject which may be predisposed to the disease but has not yet been diagnosed as having it; (b) inhibiting the disease, i.e., arresting its development; or (c) relieving the disease, i.e., mitigating or ameliorating the disease and/or its symptoms or conditions. The term "treatment" as used herein refers to both therapeutic treatment and prophylactic or preventative measures. Those in need of treatment include those already with the disorder as well as those in which the disorder is to be prevented.

As used herein, "preventative" refers to hindering or stopping a disease or condition before it occurs, even if undiagnosed, or while the disease or condition is still in the sub-clinical phase.

As used herein, "active agent" refers to a substance, compound, or molecule, which is biologically active or otherwise induces a biological or physiological effect on a subject to which it is administered to.

As used herein, "pharmaceutically acceptable carrier" refers to diluent, adjuvant, excipient, or vehicle with which an active agent, chondrocytes of the present disclosure, or composition containing chondrocytes of the present disclosure is administered in conjunction with and that is approved by a regulatory agency of the Federal or a state government or listed in the U.S. Pharmacopeia or other generally recognized pharmacopeia for use in animals and/or humans.

Unless otherwise defined herein, all technical and scientific terms used herein have the same meaning as commonly understood by one of ordinary skill in the art.

Cell Types

Exemplary cell types can include, for example, endoderm cells, hepatic progenitor cells, and hepatocytes.

Exemplars of suitable surfaces for culture vessels include but are not limited to Vitronetin, E-cadherin, Corning® Synthemax® II or Matrigel for iPSCs, include but are not limited to Matrigel for endoderm, and include but are not limited to Matrigel or Collagen for hepatic progenitor cells.

In one aspect, an exemplary method for dedifferentiating or reprogramming somatic cells can include the use of any one or more of a synthetic mRNA reprogramming factor selected from Oct4, Sox2, Klf4, cMyc, Nanog, and Lin28 and transactivation domains whereby the somatic cell is reprogrammed or de-differentiated. Methods and compositions for IPSC modulation are described in U.S. Ser. No. 13/893,166 and U.S. Ser. No. 14/292,317, the contents of which are hereby incorporated by reference.

In certain embodiments, there are protocols for the use of suspension cell cultures, and low cell-attachment culture plates and vessels can be used for such suspension cultures.

In certain embodiments, the environmental conditions such as oxygen concentration can be modulated for optimal induction conditions.

In certain embodiments, processes and methods of selection of desired cells or enhancement of their percentage confluence or cell density in the overall cell culture population are provided.

In certain embodiments, methods of cryopreservation of the hepatocyte-like cells are provided. In one embodiment, some of the differentiated cells are cryopreserved for optimal cell viability during storage. In some embodiments, HSA and DMSO can be added to the culture medium to increase cell viability during storage. In some embodiments, 2.5% HSA with 10% DMSO in culture medium can be used, for example. The cell numbers can be optimized for the further improvement of viability in storage using this application.

Re-culture differentiated cells methods are also provided. Cells can be re-cultured in most commercially available culture vessels: e.g., T75 flask, T25 flask, 6-well plate, 96-well plate. Cells can be re-cultured in different cell density for different applications.

In certain embodiments, the present disclosure also provides methods for managing physical stress on the cells thereby improving viability during handling throughout the differentiation process. Certain types of cells during the differentiation are very small, like iPSCs. These small cells are very sensitive to centrifuge force. iPSCs are very sensitive to excessive centrifuge force. Some types of cells during the differentiation are very sticky, like iPSCs and endoderm stage cells. These cells are very sensitive to sheer force. When handling these cells, a 10 mL pipet was used to avoid use any small tips and to avoid pipetting the cells up and down repeatedly. For maintenance, these cells can be cultured as colonies and then dissociated as clusters, instead of single cells. For differentiation, if single cells are necessary, one can end the dissociation prior to the cells detaching, remove the dissociation solution, and let the residual dissociation solution further dissociate the cells. This protocol is commonly used in cell culture.

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications and patents cited in this disclosure are incorporated by reference in their entirety. To the extent the material incorporated by reference contradicts or is inconsistent with this specification, the specification will supersede any such material. The citation of any references herein is not an admission that such references are prior art to the present invention.

Unless otherwise indicated, all numbers expressing quantities of ingredients, reaction conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or."

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

EXAMPLES

The invention is now described with reference to the following Examples. These Examples are provided for the purpose of illustration only, and the invention is not limited to these Examples, but rather encompasses all variations that are evident as a result of the teaching provided herein.

In some embodiments for producing mature, differentiated hepatocytes, exemplary parameters are provided in Table I, including the starting cells, culture vessels, coating, dissociation agent, medium names and major components, seeding density for an exemplary 6 well plate, and oxygen levels.

stages. Ultra-Low Attachment plates (Sigma-Aldrich) or other low attachment plates were used to encourage iPSC suspension cell growth.

When iPS cells need to be passaged, it was important to dissociate iPSC colonies with a protocol that caused low cytotoxicity and resulted in more small clusters of iPSCs, which can form spheres quickly if suspension culture is desired. iPSCs were dissociated using TripLE™ (ThermoFisher), Accutase (Life Technology), or EDTA by dissociating with EDTA of 0.1 mM, sometimes 0.5 mM, or 1 mM in DPBS (Fisher Scientific), at 37° C. for 5 minutes. Various dissociation times were used successfully, including 1 to 2 minutes, and sometimes up to 10 to 20 minutes for this step. In some embodiments, the dissociation time may be about 1,

TABLE 1

| Hepatocyte Differentiation | | | | |
|---|---|---|---|---|
| | 2-6 days Stage 1 | 1-3 days Stage 2 | 1-3 days Stage 3 | 3-6 days Stage 4 |
| Starting Cells | iPSCs | Endoderm | Hepatic Progenitor Cells | Hepatocytes |
| Culture Vessels | Culture Plate/ Flask Flask | Culture Plate/ Flask | Culture Plate/ Flask | Culture Plate/ Flask |
| Coating | None | Matrigel | Matrigel/ Collagen I | Matrigel/ Collagen I |
| Dissociation | EDTA | TypLE | TypLE | TypLE |
| Medium Names and Main Components | MEMa, DMEM/F12, DMEM B27 10-50 uM Insulin 5% KSR FoxA2 or SOX17 mRNA transfection | MEMa, DMEM/F12, DMEM B27 With or without 1% DMSO Hex, Tbx3, or GATA4, GATA6 mRNA transfection | MEMa, DMEM/F12, DMEM B27 HNF1a, HNF4a, HNF6, CEB/Pa, CEB/Pb mRNA transfection | Hepatocyte medium |
| Seeding Density (For 6-well Plate) | $1 \times 10^5 - 4 \times 10^5$ cells per well | $1 \times 10^5 - 3 \times 10^5$ cells per well | $3 \times 10^5$ cells per well | $3 \times 10^5$ cells per well |
| Oxygen | Normal Oxygen | Normal Oxygen | Normal Oxygen | Normal Oxygen |

Example 1: Generating Endoderm Cells from iPSCs iPSCs were plated into standard size 6-well cell culture plates (about 9.5 cm² growth area/well) or standard size 12-well cell culture plates (about 3.8 cm² growth area/well) to begin differentiation. Other sized culture vessels are optionally applicable as well and sometimes may be more preferred over 6-well or 12-well plates because of higher efficiency of the use of reagents and time.

In a 6-well plate (standard commercially available), cells of a population size from $1 \times 10^5$ to $4 \times 10^5$ per well have been successfully used. iPSCs were considered ready for differentiation when there were enough typical iPSCs colonies with sharp well-defined edges, where the cells are compact, and colonies were not overgrown. The quality of iPSC's of the present invention produced using these criteria proved to be critical for differentiation when the iPSC lines of the present invention were compared with iPSC lines that were produced by others using other methods.

iPSCs at this stage were induced to differentiate into mesendoderm lineage cells. It was discovered that suspension culture systems were very useful for scaling up at this stage even though most current protocols for differentiation prefer to use attached monolayer cells. It was found that iPSCs grown in suspension for induction were more resistant to chemical toxicity and were easier to re-plate in later 2, 3, 4, 5, 6, 7, 8, 9, 10, 11, 12, 13, 14, 15, 16, 17 18, 19, 20, or 25 minutes, or any time range between any two of the recited times.

For medium, MEMa, DMEM/F12, and DMEM B27 were tested with 10-50 uM insulin and 5% KSR and the results as desired were achieved at this stage of differentiation. iPSCs were then induced to leave the pluripotent stage and differentiate towards mesendoderm by the presence of GSK3 inhibitors such as CHIR99021, CHIR98014, BIO or GSK inhibitor IX, and SB-216763, which de-repress the functions of the Wnt, BMP4, and Activin A pathway genes. In some aspects the concentration of insulin may be, for example, about 10, 11, 12, 13, 14, 15, 16, 17, 18, 19, 20, 25, 30, 35, 40, 45, or 50 uM, or any value or range between any two of the recited concentrations. The GSK3 inhibitors were performed in a 1-, 2-, 3-day time windows and used FoxA2, CXCR4 positive cell counts as quality analysis when choosing time and concentrations of the inhibitors of, for example, 5 mM, 8 mM, 10 mM, etc.

Figure 1B:
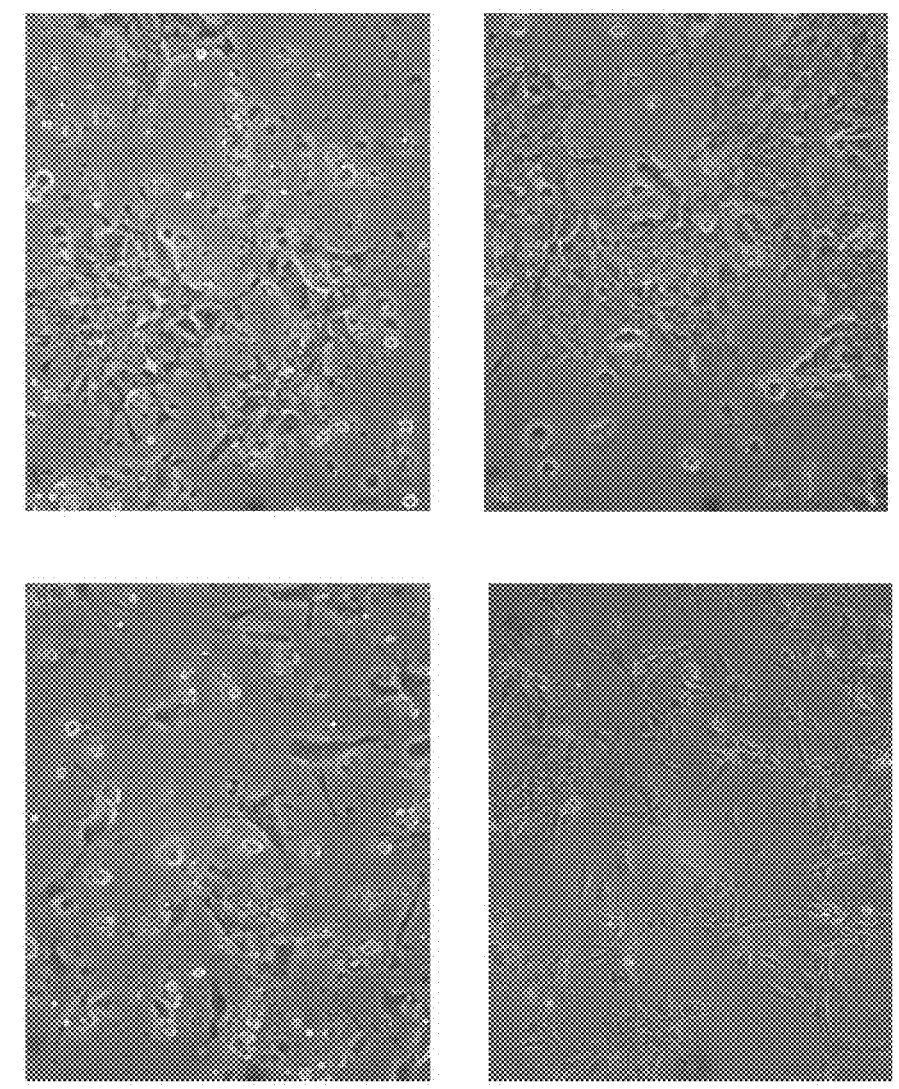
FIG. 1B shows endoderm cells induced from iPSCs by using Sox17 mRNA at various densities (e.g. from low to high density as described in the Example) and illustrates an exemplary embodiment of endoderm induction.

In one experiment, cells were then transfected with FoxA2, and/or Sox17 mRNA at a dose of about 20 ng per well with Stemgent Transfection Reagent (Stemgent). This transfection was also performed including GATA4 mRNA, and/or GATA6 mRNA, and was repeated for 3, 4, 5 and 6 times, sometimes at a dose of mRNA 10 times higher, using Stemgent Transfection Reagent or other commercially available transfection reagents. Cells at this stage showed morphology that were closer to epithelial cells than mesenchymal cells, derived from iPSCs from different mRNA transfection times and starting density (FIG. 1).

In another experiment, as an alternative to the process outlined in Table 1, iPSC cells grown as spheres in suspension were transfected directly using electroporation, (for example, using MaxCyte STX electroporator) without plating on the surface of a plate. In one embodiment, 2 million starting iPSCs in spheres were transfected in suspension with different mRNA, e.g. Sox17 or Pax6, or mock transfected. The mRNA amount tested in FIG. 8 was 2500 ng. Cells were then grown in NBM in the case of Sox17 transfection, or MEMalpha with KSR in the case of Pax6 transfection. Transfection can be repeated 1, 2, 3, 4, 5 or even more times if the transition takes longer period of time. As result, after the 1st transfection of Sox17 mRNA, the cell clusters became significantly smaller and less compact spheres, losing defined "edge" or outer boundary. In contrast, mock-transfected spheres maintain well-defined, showing clearly visible outer "edge" in 2D photos. The smaller spheres of the untransfected or mock-transfected iPSCs have a transparent appearance, whereas the bigger ones look less transparent for being thick in cell layers. For comparison, iPSC spheres transfected with Pax6 (a neural differentiation TF) mRNA progressed towards ectoderm, i.e. neural progenitor cells, of which the spheres became darker and had less sharp "edge" than mock-transfected, but were bigger in size and had more defined boundaries than the Sox17 transfected.

By the same principle and similar methods, germ layer-specific intermediate cells such as endoderm cells, and more downstream intermediate cells such as hepatic progenitor cells, pancreatic progenitor cells, etc., can also be transfected with additional TF mRNAs in spheres. Cells transfected this way are more resistant to toxicity from small molecules, growth factors, or other elements in cell cultures, and should be in general more efficient in differentiation than 2D transfection using chemical reagents. This observation, unseen in scientific publication, was made inadvertently during a testing of an electroporation equipment, and served as an enabling method as part of the current disclosure.

Example 2: Generating Hepatic Progenitor Cells from Endoderm Cells

Figures 2A, 2B, 2C:
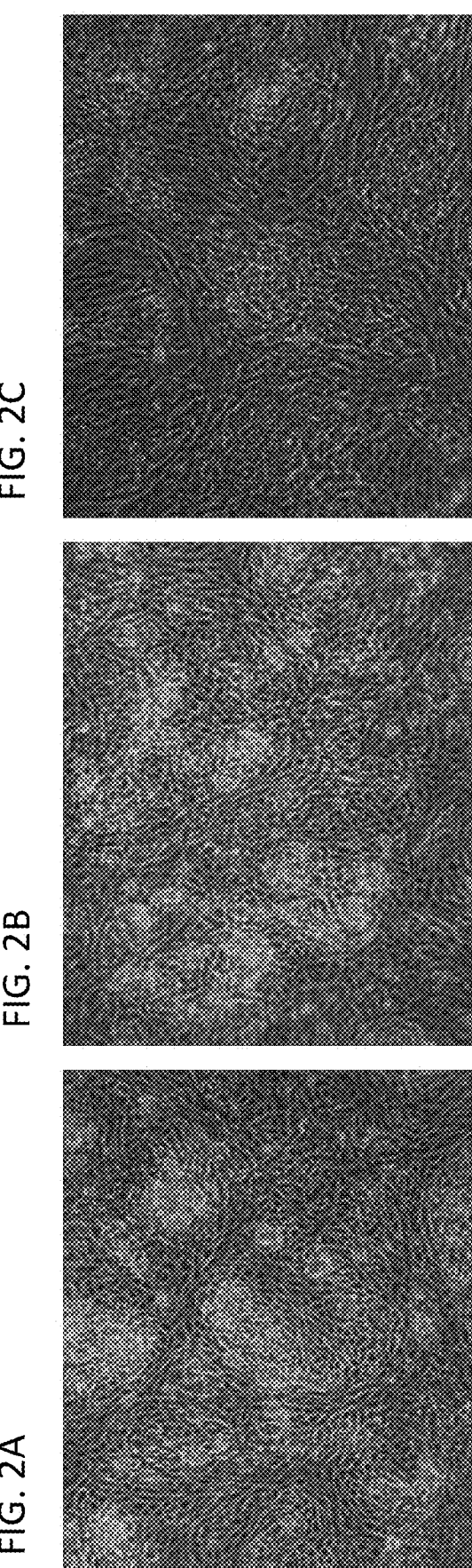
FIG. 2A shows an exemplary view of cell density/cluster associated with the induction.
FIG. 2B shows an exemplary view of cell density/cluster associated with the induction.
FIG. 2C shows an exemplary view of cell density/cluster associated with the induction.

Endoderm cells are plated on commercial cell culture vessels. 6-well plates were used in experiments shown in FIG. 2, but other well sizes are applicable. Plates were pre-coated with Matrigel (BD Biosciences), $1\times10^5$-$1\times10^6$ cells were then plated in DMEM/F12 or MCDB131 supplemented with 8 mM D-glucose. Sometimes adding 1% DMSO at this stage was observed to helpful for increasing the efficiency of generating hepatic progenitor cells.

In one experiment, cells were then transfected with Hex and/or Tbx3 mRNA. Additionally, the cells were transfected or co-transfected, for stronger effects, with mRNA for GATA4, GATA6 mRNA at a dose of 50 ng per well with Stemgent Transfection Reagent (Stemgent) in culture medium, and repeated for 2, 3, or more times, at doses at low as 10 ng and as high as 200 ng per well, using Stemgent Transfection Reagent or other commercially available transfection reagents. In some aspects the Stemgent concentration may be, for example, about 10, 20, 30, 40, 50, 60, 70, 80, 90, 100, 110, 120, 130, 140, 150, 160, 170, 180, 190, or 200 ng per well, or any amount between any two of the recited amounts. This amount may also be adjusted for other well volumes. The cells at this stage appear darker than endoderm cells and tended to form clusters of hepatic progenitor cells (FIG. 2).

Example 3: Generating Hepatocytes from Hepatic Progenitor Cells

Hepatic progenitor cells were cultured in 6-well or other plates pre-coated with Matrigel (BD Biosciences) or Collagen I (Sigma) in DMEM/F12, MEMa, or DMEM B27. Other similar attachment cell culture medium is also suitable for use.

Figure 3:
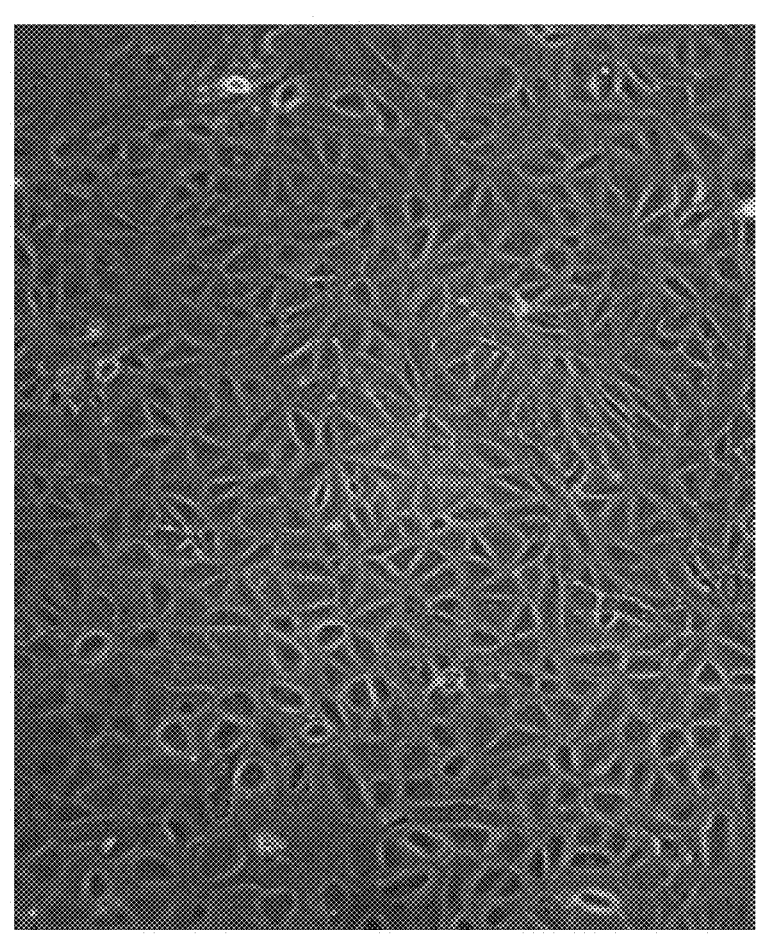
FIG. 3 shows hepatocytes derived directly from hepatic progenitor cells in monolayer culture and illustrates an exemplary embodiment of hepatocyte induction.

Hepatic progenitor cells were further transfected with HNF1a, HNF4a, HNF6, CEB/Pa, or CEB/Pb mRNA at a dose of 10-200 ng per well with Stemgent Transfection Reagent (Stemgent) in culture medium supplemented with 200 ng/mL B18R. The dose of Stemgent may also be about 10, 20, 30, 40, 50, 60, 70, 80, 90, 100, 110, 120, 130, 140, 150, 160, 170, 180, 190, or 200 ng per well, or any amount between any two of the recited amounts. This amount may also be adjusted for other well volumes. Most commercially available transfection reagents are also applicable. Hepatocytes were obtained at this stage by passing the progenitor cells to lower density in hepatocyte medium (FIG. 3).

Example 4: Hepatocytes in 3-Dimensional Spheres

Figure 4:
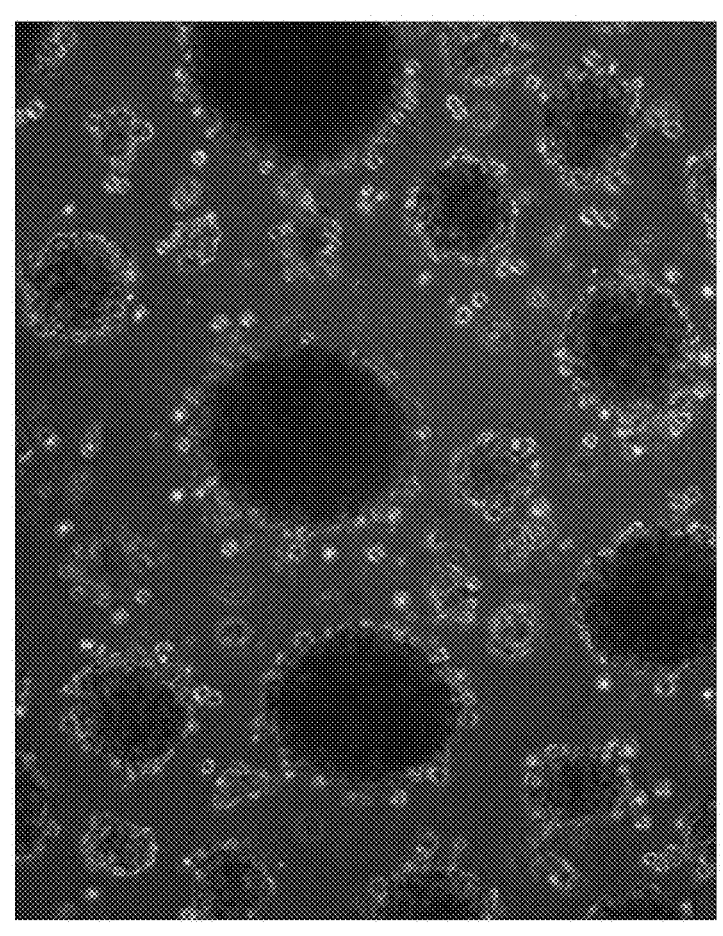
FIG. 4 shows hepatocyte progenitor cells grown as 3-dimensional (3D spheres, which matures into hepatocytes, and illustrates an exemplary embodiment of hepatocyte maturation in 3D spheres.

Instead of dissociation and replating, hepatic progenitor cells were allowed to continue to grow for 1 week to 2 months, or even longer, during which time clustered progenitor cells continuously formed 3 dimensional (3D) spheres and moved into suspension (FIG. 4).

Figure 5B:
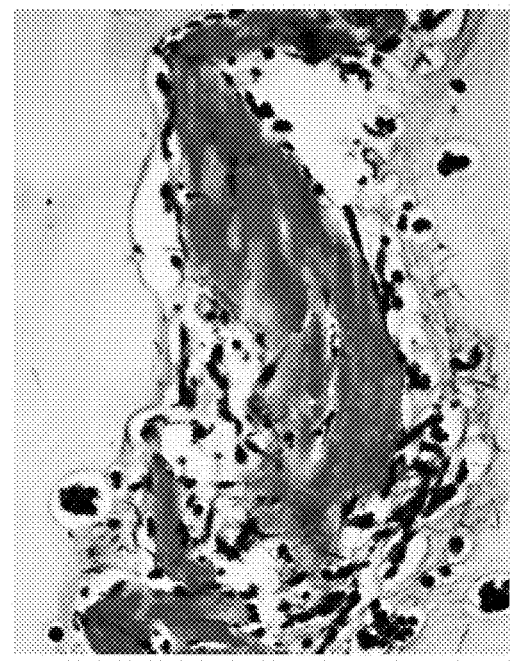
FIG. 5B shows an exemplary view of hepatocyte/glycogen.
Figure 5A:
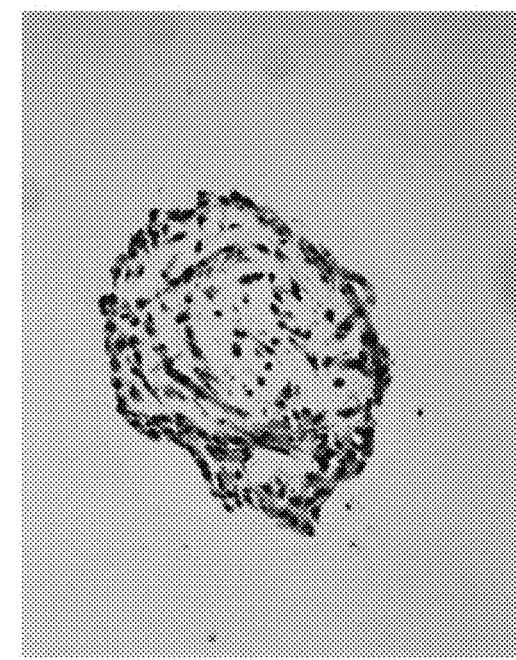
FIG. 5A shows an exemplary view of hepatocyte/glycogen.
Figure 6B:
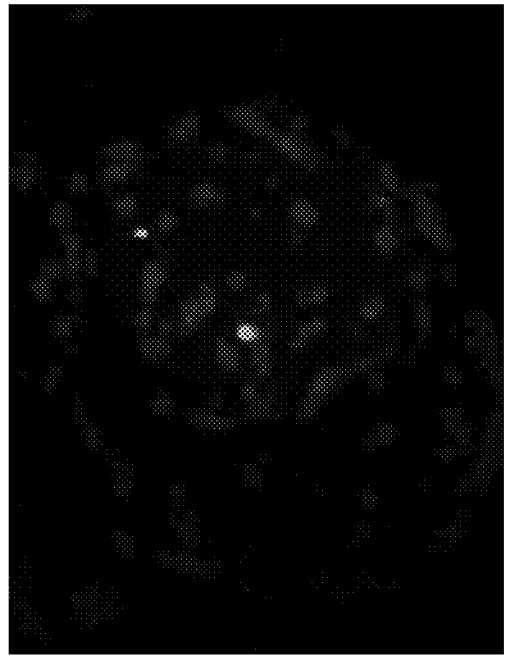
FIG. 6A shows AFP staining and FIG. 6B shows A1 anti-trypsin.
Figure 6A:
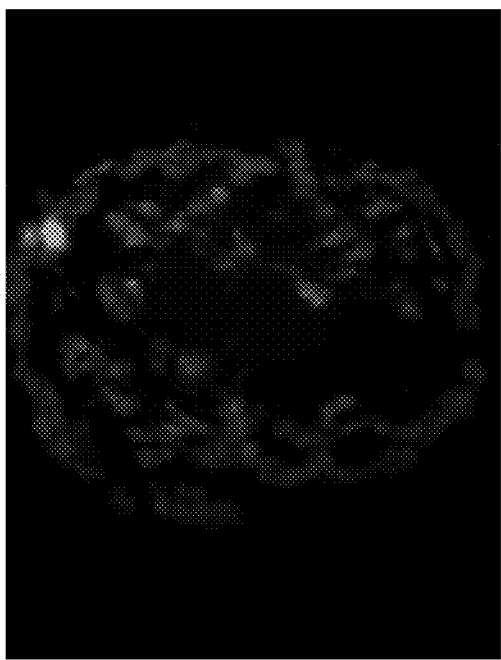

The cells in 3D at this stage were tested by expression of glycogen (FIG. 5), and liver cell marker staining by antibodies (FIG. 6). The positive staining of glycogen, AFP, trypsin confirmed that the cells have reached mature stage of liver cells.

Figure 7:
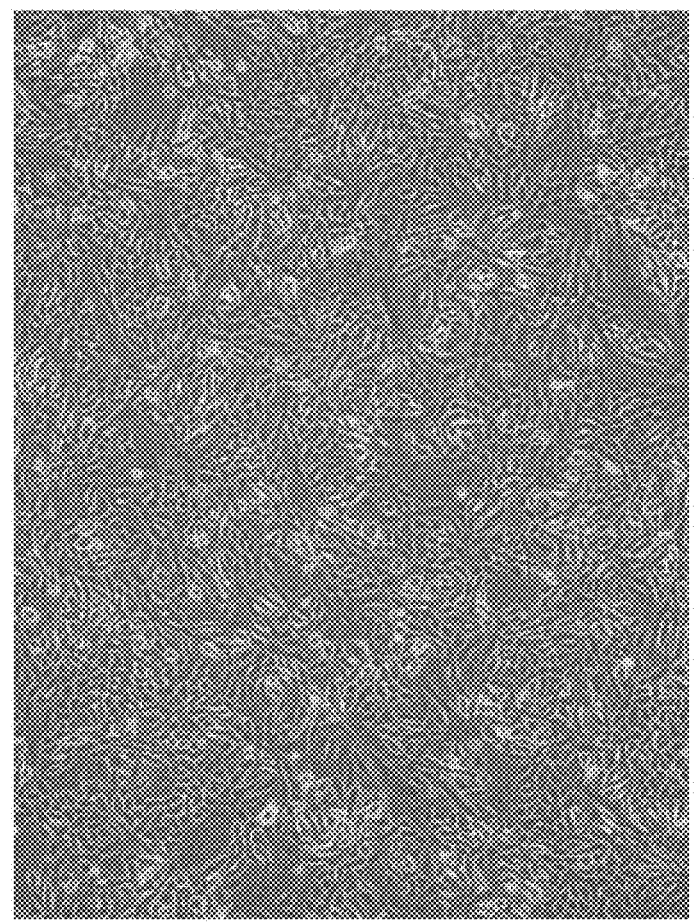
FIG. 7 shows hepatocytes derived directly from 3D hepatic progenitor cell spheres replated as monolayer culture and illustrates an exemplary embodiment that human hepatocytes created through 3D spheres can be replated into monolayer and display mature hepatocyte morphology.

These hepatocytes in 3D spheres were dissociated with Accutase, TrypLE or other dissociation reagents, and replated to coated surface as in Example 3. They immediately showed terminally differentiated morphology of hepatocytes, without further division in a monolayer culture (FIG. 7).

Example 5: iPSC-Derived Hepatocytes Function in Animal Models

To further test the functions of the mature hepatocytes produced according to the present invention, the liver function of the iPSC-derived hepatocytes are tested in liver disease or injury mouse models such as: 1) Surgical bile duct ligation (BDL) mouse model for cholestatic liver injury, 2) MDR2/Tgfbr2/Il2ra genetically modified mouse models for cholestatic liver injury, 3) DDC-modified diet, ANIT-modified diet or d-galactosamine-induced mouse model as alternative for cholestatic liver injury, 4) Hypercaloric Diets induced mouse model for NASH liver injury, 5) ob/ob, nSREBP-1c or PTEN genetically modified mouse model for NASH liver injury, 6) MCDD/CDAA mouse model as alternative for NASH liver injury, or 7) CCl4/TAA/DEN/DMN induced mouse model for toxic liver injury.

Additionally, ALD (Alcohol-induced), autoimmune hepatitis (AIH) and virus infectious liver diseases are all major public health issues that the hepatocytes generated by the current invention can address through transplant, including the use of animal models.

Non-human Primate Models such as: 1) Hypercaloric Diets induced monkey liver injury model, 2) CCl4 induced monkey liver injury model, 3) BDL monkey liver injury model are used to test the functions of the disclosed hepatocytes.

Delivery route: hepatocytes or spheres are infused into the liver.

Testing: measurements are taken for blood levels of albumin, AST, ALT, Bilirubin and Hyaluronan (week 2, 4, 8, 12, 16, 24); measurements are taken for blood levels of pro-inflammatory cytokines, like IL-8, TNFa, MCP-1 (week 2, 4, 8, 12, 16, 24); IHC of transplant site for Fibrosis, Hepatocyte, Kupffer cells/macrophages, and HCC markers are performed.

Example 6: iPSC-Derived Hepatocytes in Treating Human Patients with Liver Diseases Such Chronic Liver Failure Clinical trials using human iPSC-derived hepatocytes using the disclosed protocols adapted to suit under cGMP procedures are dosed according to animal studies with reference to other cell therapies. The manufactured liver cells or mini-organs based on 3D liver cells are delivered to liver, or other parts of the human body such as muscles, connective tissues, or certain sites of other organs to achieve efficacy.

The invention claimed is:

1. A method of inducing differentiation of stem cells into hepatocytes, comprising the steps of:
   (a) culturing induced pluripotent stem cells as starting cells;
   (b) inducing differentiation of said starting cells into a mesendoderm lineage;
   (c) generating endoderm cells by culture cell transfection of the said mesendoderm lineage cells with a first combination of mRNAs encoding endodermal differentiation factors, wherein the first combination of mRNAs comprises FoxA2 or Sox17 mRNAs;
   (d) generating hepatic progenitor cells by culture cell transfection of said endoderm cells with a second combination of mRNAs encoding hepatic progenitor cell differentiation factors, wherein the second combination of mRNAs comprises one or more of Tbx3, GATA4, GATA6, and Hex mRNAs;
   (e) generating hepatocytes by culture cell transfection of said hepatic progenitor cells with a third combination of mRNAs encoding hepatocyte maturation factors to form cell clusters, wherein the third combination of mRNAs comprises one or more of HNF4a, HNF1a, HNF6, CEB/Pa, and CEB/Pb mRNAs;
   wherein the differentiation factors of steps (c) and (d), and the maturation factors present in the cell cultures of step (e) consist of transcription factors introduced by mRNA transfections; wherein steps (c) to (e) do not employ polypeptide growth factors in the culture medium that guide generation of hepatocytes; and
   (f) obtaining said hepatocytes by collecting said clusters formed from said hepatic progenitor cells and replating said clusters to obtain monolayers of hepatocytes.

2. The method of claim 1, wherein said first combination of mRNAs comprises FoxA2 mRNAs.

3. The method of claim 1, wherein said first combination of mRNAs comprises Sox17 mRNAs.

4. The method of claim 1, wherein said first combination of mRNAs comprises FoxA2 and Sox17 mRNAs.

5. The method of claim 1, wherein said first combination of mRNAs comprises FoxA2, Sox17, GATA4, and GATA6 mRNAs.

6. The method of claim 1, wherein said second combination of mRNAs comprises Hex mRNAs.

7. The method of claim 1, wherein said second combination of mRNAs comprises Tbx3 mRNAs.

8. The method of claim 1, wherein said second combination of mRNAs comprises Tbx3 and Hex mRNAs.

9. The method of claim 1, wherein said second combination of mRNAs comprises Tbx3, GATA4, GATA6, and Hex mRNAs.

10. The method of claim 1, wherein said third combination of mRNAs comprises HNF1a mRNAs.

11. The method of claim 1, wherein said third combination of mRNAs comprises HNF4a mRNAs.

12. The method of claim 1, wherein said third combination of mRNAs comprises HNF4a, HNF1a, HNF6, CEB/Pa, and CEB/Pb mRNAs.

13. The method of claim 1, wherein said starting cells are harvested from a body fluid or tissue of a subject.

14. A method of producing differentiated hepatocytes from induced pluripotent stem cells, comprising the steps of:
   (a) culturing said induced pluripotent stem cells as starting cells;
   (b) inducing differentiation of said starting cells into a mesendoderm lineage;
   (c) generating endoderm cells by culture cell transfection of said mesendoderm lineage cells with a first combination of mRNAs encoding endodermal differentiation factors, wherein the first combination of mRNAs comprises FoxA2 or Sox17 mRNAs;
   (d) generating hepatic progenitor cells by transfection of said endoderm cells with a second combination of mRNAs encoding hepatic progenitor cell differentiation factors, wherein the second combination of mRNAs comprises one or more of Tbx3, GATA4, GATA6, and Hex mRNAs;
   (e) generating hepatocytes by transfection of said hepatic progenitor cells with a third combination of mRNAs encoding hepatocyte maturation factors to form cell clusters, wherein the third combination of mRNAs comprises one or more of HNF4a, HNF1a, HNF6, CEB/Pa, and CEB/Pb mRNAs;
   wherein differentiation factors of steps (c) and (d), and maturation factors of step (e) consist of transcription factors introduced by mRNA transfections, wherein steps (c) to (e) do not employ polypeptide growth factors in the culture medium that guide generation of hepatocytes; and
   (f) obtaining said hepatocytes by passaging said clusters into monolayers to obtain hepatocytes or collecting said clusters formed from said hepatic progenitor cells and replating said clusters to obtain monolayers of hepatocytes.

15. A method for producing endoderm cells from induced pluripotent stem cells, comprising the steps of:
   (a) culturing said induced pluripotent stem cells as starting cells;
   (b) inducing differentiation of said starting cells into a mesendoderm lineage; and
   (c) generating endoderm cells by culture cell transfection of said mesendoderm lineage with a combination of mRNAs encoding endodermal differentiation factors comprising FoxA2 and/or Sox17 mRNAs in an effective dose and within specific time windows, and wherein the differentiation factors consist of transcription factors introduced by mRNA transfections, and polypeptide growth factors in the culture medium that guide generation of endoderm cells are not employed.

16. The method of claim 1, wherein the hepatocytes are footprint-free.

17. The method of claim 1, wherein steps (c) to (e) do not employ type-specific growth factor proteins in the culture medium.

18. The method of claim 14, wherein the hepatocytes are footprint-free.

19. The method of claim 14, wherein steps (c) to (e) do not employ cell type-specific growth factor proteins in the culture medium.

20. The method of claim 15, wherein the endoderm cells are footprint-free.

21. The method of claim 15, wherein step (c) does not employ endoderm-specific growth factor proteins in the culture medium.

22. The method of claim 1, wherein
the first combination of mRNAs consists of FoxA2 mRNAs, or Sox17 mRNAs, or FoxA2 mRNAs and Sox17 mRNAs, or FoxA2 mRNAs, Sox17 mRNAs, GATA4 mRNAs, and GATA6 mRNAs;
the second combination of mRNAs consists of Hex mRNAs, or Tbx3 mRNAs, or Hex mRNAs and Tbx3 mRNAs, or Tbx3, GATA4, GATA6, and Hex mRNAs; and
the third combination of mRNAs consists of HNF1a mRNAs, or HNF4a mRNAs, HNF4a mRNAs, HNF1a mRNAs, HNF6 mRNAs, CEB/Pa, and CEB/Pb mRNAs.

* * * * *